(12) United States Patent
Nakahara

(10) Patent No.: US 9,107,582 B2
(45) Date of Patent: Aug. 18, 2015

(54) OPHTHALMOLOGIC APPARATUS, CONTROL METHOD FOR OPHTHALMOLOGIC APPARATUS, AND PROGRAM

(71) Applicant: CANON KABUSHIKI KAISHA, Tokyo (JP)

(72) Inventor: Yasuhiro Nakahara, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 91 days.

(21) Appl. No.: 13/967,420

(22) Filed: Aug. 15, 2013

(65) Prior Publication Data

US 2014/0063448 A1 Mar. 6, 2014

(30) Foreign Application Priority Data

Aug. 30, 2012 (JP) ................................. 2012-190585

(51) Int. Cl.
*A61B 3/00* (2006.01)
(52) U.S. Cl.
CPC .................................... *A61B 3/0083* (2013.01)
(58) Field of Classification Search
CPC .......... A61B 3/14; A61B 3/10; A61B 5/0073; A61B 3/0083

USPC ........... 351/206, 208, 210, 205, 246; 356/479
See application file for complete search history.

(56) References Cited

U.S. PATENT DOCUMENTS

| | | | | |
|---|---|---|---|---|
| 2008/0100801 | A1* | 5/2008 | Yahagi et al. | 351/206 |
| 2010/0296057 | A1* | 11/2010 | Nagashio et al. | 351/208 |
| 2012/0249961 | A1* | 10/2012 | Muto | 351/208 |

FOREIGN PATENT DOCUMENTS

JP 3507204 B2 3/2004

* cited by examiner

*Primary Examiner* — Hung Dang
(74) *Attorney, Agent, or Firm* — Carter, DeLuca, Farrell & Schmidt, LLP

(57) ABSTRACT

Provided is an ophthalmologic apparatus capable of efficiently switching between an attitude for packing and an attitude for eye examination. When a USB communication between the ophthalmologic apparatus and a PC for control is disconnected, an attitude of the ophthalmologic apparatus is switched from the attitude for eye examination to the attitude for packing. Even when the USB communication between the ophthalmologic apparatus and the PC for control is established, if there is no operation for a certain period of time, the attitude for eye examination is switched to the attitude for packing. When power of the ophthalmologic apparatus is turned off, the attitude for eye examination is switched to the attitude for packing, using a spare power supply provided to a main body of the ophthalmologic apparatus.

9 Claims, 22 Drawing Sheets

OPHTHALMOLOGIC APPARATUS, CONTROL METHOD FOR OPHTHALMOLOGIC APPARATUS, AND PROGRAM

BACKGROUND OF THE INVENTION

1. Field of the Invention

The present invention relates to an ophthalmologic apparatus, a method for controlling an attitude of an ophthalmologic apparatus, and a program therefor.

2. Description of the Related Art

In an ophthalmologic apparatus, in recent years, there is a tendency to incorporate various functions for aiding diagnosis and automate measurement.

As the functions are increased, there is a tendency that the number of operation members of the main body portion is also increased. A size of the main body portion is inversely proportional to the increase of the number of operation members. An operation portion of the main body is operated manually by an examiner. Therefore, there is a limitation in downsizing the operation portion. As a result, the operation portion unit is upsized in proportion to the number of operation members. When the operation portion unit is upsized, a size of the upsized operation portion unit may determine a size of the main body. Therefore, when the number of operation members is increased, there is a case where the operation portion is separated from the main body portion, and the operation portion is connected to the main body with a cable or the like so that the main body portion becomes compact (see Japanese Patent No. 3507204). Alternatively, there is a method of eliminating the operation members of the main body portion and connecting the main body portion to a personal computer (PC) for control so as to operate the apparatus using a graphical user interface (GUI) of the PC. When the operation portion is the GUI, a pointing device is used for operation. Therefore, the operation portion can be arranged in a denser manner than a case where the operation portion is formed of hardware. As a result, the main body portion can be very simple because the operation portion is eliminated.

In an automatic measurement, it is necessary to electrically drive the main body portion. As a result, when power to the main body is turned off, an attitude of the main body portion cannot be changed manually. This restriction causes an inconvenience in eye examination or in transportation because it is difficult to efficiently switch between a waiting attitude before eye examination and an attitude when the main body is packed and transported.

However, in the invention disclosed in Japanese Patent No. 3507204, only an example of the waiting attitude before eye examination is described. Therefore, when power of the main body or power of the PC for control is turned off, an attitude of the main body portion cannot be freely changed unlike the conventional one. Therefore, it is necessary to turn on the power again so that the main body is set to have the attitude for packing and transporting. In the case of the main body to which the PC for control is connected for its attitude control, if power of the PC is turned off, it is necessary to power on the PC again so as to change the attitude of the main body. In this case, it takes time to restart an OS installed in the PC. Further, if the cable is disconnected when it becomes necessary to change the attitude for packing, more time may be wasted for reconnecting the cable than for restarting the OS.

SUMMARY OF THE INVENTION

The present invention has been made to solve the above-mentioned problem, and it is an object thereof to provide an ophthalmologic apparatus that is capable of efficiently switching between an attitude for eye examination and an attitude for packing, and to provide a control method for an ophthalmologic apparatus and a program therefor.

According to one embodiment of the present invention, there is provided an ophthalmologic apparatus, which is to be controlled by a separable control device, the ophthalmologic apparatus including:

an optical head unit portion for photographing an image of an eye to be inspected in accordance with a command from the control device;

an optical head unit drive portion for driving the optical head unit portion with respect to the eye to be inspected;

a chin rest unit portion for defining a height of the eye to be inspected in accordance with a command from the control device;

a chin rest unit drive portion for driving the chin rest unit portion with respect to the optical head unit portion;

a sub control apparatus different from the control device; and a status determination unit for determining a status of the ophthalmologic apparatus, in which the sub control apparatus controls, in accordance with a result of the determination by the status determination unit, the optical head unit drive portion and the chin rest unit drive portion to drive the optical head unit portion and the chin rest unit portion to one of a first predetermined position and a second predetermined position different from the first predetermined position.

According to another embodiment of the present invention, there is provided a control method for an ophthalmologic apparatus that is to be controlled by a separable control device and includes an optical head unit portion for photographing an image of an eye to be inspected and a chin rest unit portion for defining a height of the eye to be inspected with respect to the optical head unit portion when photographing, the control method including:

determining a communication status between the ophthalmologic apparatus and the control device; and driving, by a sub control apparatus of the ophthalmologic apparatus, the optical head unit portion and the chin rest unit portion to one of a first predetermined position and a second predetermined position different from the first predetermined position in accordance with a result of the determination of the communication status.

According to the embodiments of the present invention, the ophthalmologic apparatus can efficiently switch its attitude between the attitude for eye examination and the attitude for packing.

DESCRIPTION OF THE EMBODIMENTS

First Embodiment

Figure 1:
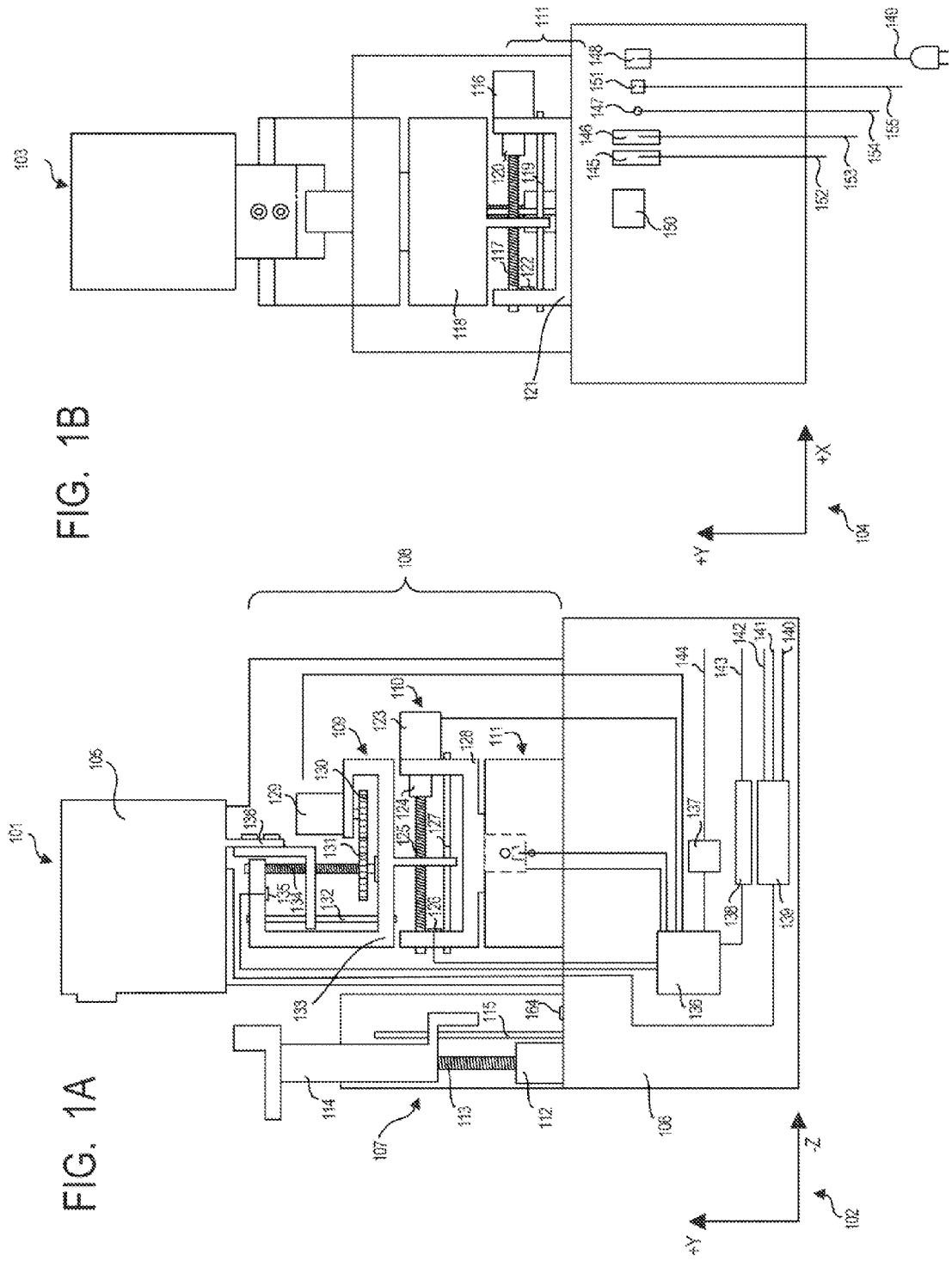
FIGS. 1A and 1B are block diagrams of an ophthalmologic apparatus according to a first embodiment of the present invention.
Figure 2:
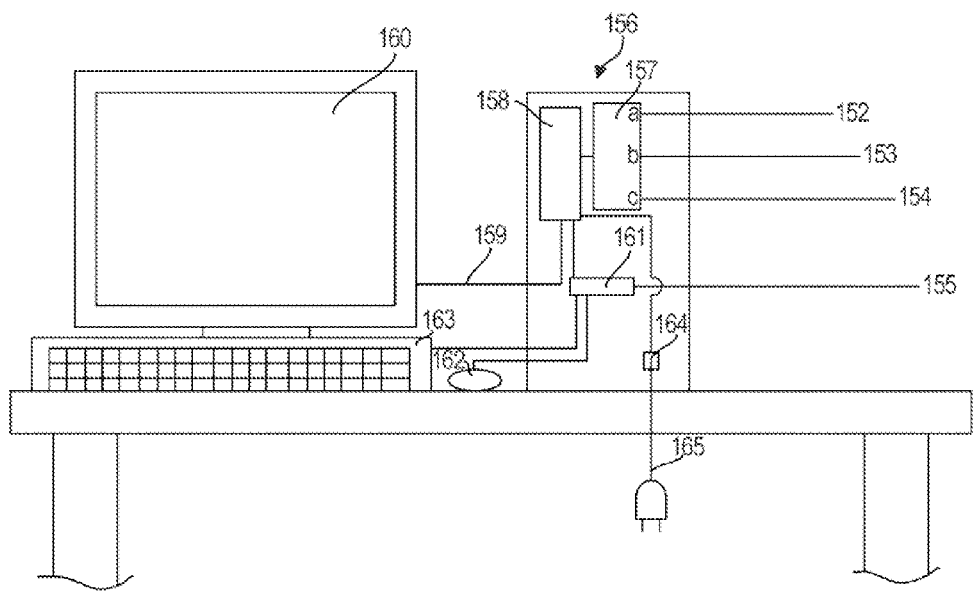
FIG. 2 is a block diagram of a PC for control, which is configured to control the ophthalmologic apparatus according to the first embodiment of the present invention.

An ophthalmologic apparatus according to a first embodiment of the present invention is described with reference to FIGS. 1A, 1B and 2. FIGS. 1A and 1B are block diagrams of the ophthalmologic apparatus. FIG. 2 is a block diagram of a PC that is a control device for processing an optical signal obtained by the ophthalmologic apparatus and controlling an attitude of the apparatus.

FIG. 1A illustrates a front view 101 of the ophthalmologic apparatus for photographing an anterior ocular segment image, a fundus image, and an ophthalmic tomography image, and a coordinate system 102 of the front view 101. FIG. 1B also illustrates a side view 103 of the ophthalmologic apparatus, and a coordinate system 104 of the side view 103.

An optical head unit portion 105 (hereinafter referred to as optical head portion) is a unit for converting optical information of an eye to be inspected (not shown) into electronic data or an optical interference signal so as to photograph an image of the eye to be inspected in accordance with a command from a PC 156 described later. The optical information of the eye to be inspected is received from an objective lens (not shown), and the optical information is divided by a half mirror or the like. Thus, the anterior ocular segment image, the fundus image, and the ophthalmic tomography image are observed simultaneously. The optical information of an anterior ocular segment of the eye to be inspected (not shown) is converted into electronic data by a solid state image sensor unit such as a charge coupled device image sensor (CCD) (not shown), for example. The optical information of a fundus portion of the eye to be inspected (not shown) is converted into an optical interference signal by a scanning laser ophthalmoscope (SLO) unit (not shown) or the like, for example. The ophthalmic tomography image of the eye to be inspected (not shown) is converted into an interference signal by an optical fiber unit (not shown).

A base unit portion 106 supports the optical head portion 105, an XYZ unit portion 108, and a chin rest unit portion 107. The base unit portion 106 includes a USB hub unit 137, a CPU unit 136, a power supply unit 138, and a line sensor unit 139.

As to power supply, an AC power is supplied to the power supply unit 138 via a power cord 149, an AC inlet 148, a power switch 150, and a wiring 143. The power supply unit 138 converts the AC power into a DC power and supplies the DC power to a drive portion (not shown) in the optical head unit portion 105 and a unit for performing an electric process via the CPU unit 136.

Prior to description of the line sensor unit 139, a term "camera link" is described. The camera link is a standard specification for connecting an industrial digital camera to an image input board. The standard specification is drawn up by U.S. Automated Imaging Association.

The line sensor unit 139 is a unit for measuring light intensity for each wavelength to be converted into electronic data by dispersing the optical interference signal of the tomographic image of the eye to be inspected from the optical head unit portion 105 by a waveguide (not shown). The line sensor unit 139 includes a wiring 140 connected to a camera link connector 145, a wiring 141 connected to a camera link connector 146, and a wiring 142 connected to a camera link synchronization connector 147.

Prior to description of connection of the camera link connector 145, the camera link connector 146, and the camera link synchronization connector 147 to the PC 156, a camera link board 157 is described first, which is inserted to a peripheral component interconnect (PCI) slot (not shown) of the PC 156. On the camera link board 157, there are mounted two camera link connectors (157(a) and 157(b)), and a camera link synchronization connector 157(c).

A connector cable 152 is a cable for connecting the camera link connector 145 to the camera link connector 157(a).

A connector cable 153 is a cable for connecting the camera link connector 146 to the camera link connector 157(b).

A connector cable 154 is a cable for connecting the camera link synchronization connector 147 to the camera link synchronization connector 157(c).

The CPU unit 136 has the following functions:

1. Transferring the image signal of the anterior ocular segment of a subject (not shown) photographed by the CCD (not shown) to the USB hub unit 137;

2. Controlling a drive portion or a sensor portion of the XYZ unit 108 based on a control signal from a GUI interface; and 3. Counting time by a real time clock circuit (not shown).

In addition, the CPU unit 136 includes a module region having a function as a sub control apparatus in the present invention different from the above-mentioned PC, and a module region having a function as a status determination unit for determining a status of the ophthalmologic apparatus including a communication status with the PC.

The USB hub unit 137 transfers an XYZ control signal from the PC 156 to the CPU unit 136 and transfers the image signal of the anterior ocular segment from the CPU unit 136 to the PC 156.

A wiring 144 is a cable for connecting the USB hub unit 137 to a USB connector terminal 151.

A USB connector cable 155 is a cable for connecting the USB connector terminal 151 to a USB connector terminal 161.

Figure 5:
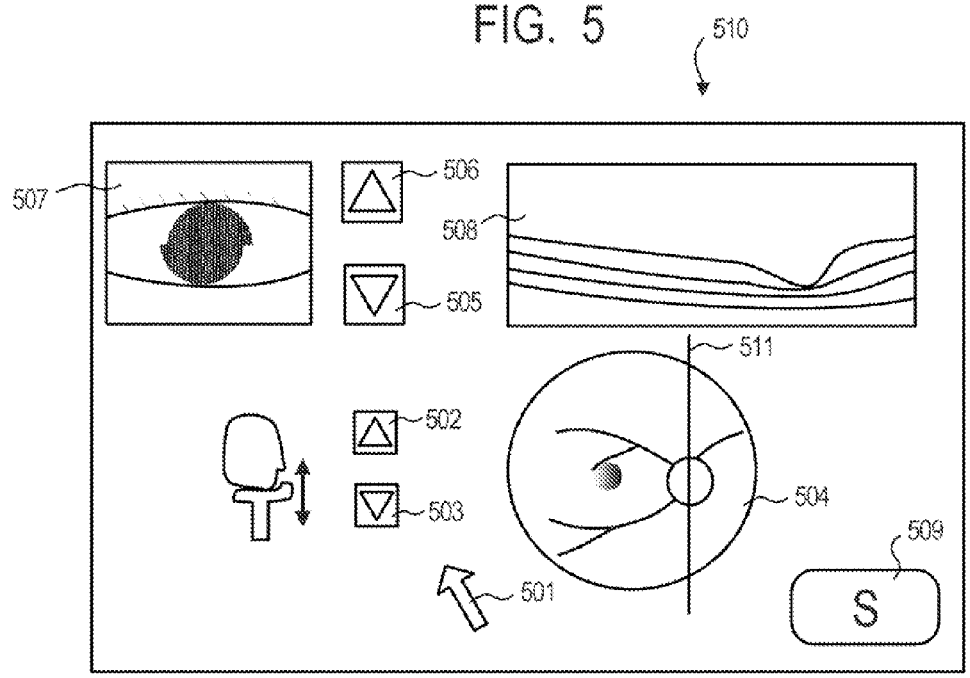
FIG. 5 is a screen of GUI application software (GUI app).

FIG. 5 illustrates a screen of GUI application software (GUI app). The GUI app is application software working on an OS of the PC 156 (not shown) described later. A display portion 510 of a display 160 is described later. A mouse cursor 501 is operated by a mouse 162 described later. A button 503 is provided for lowering the chin rest unit portion 107. When an anterior ocular segment displayed area 507 of the eye to be inspected is clicked, the optical head portion 105 moves in an X direction or in a Y direction in accordance with the clicked area. Details are described below with reference to FIG. 6.

Figure 6:
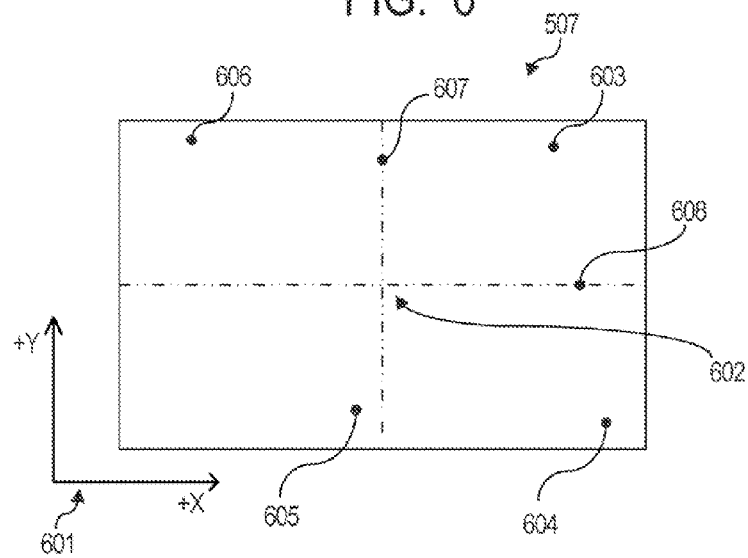
FIG. 6 is a diagram illustrating details of an operation method of an optical head portion.

FIG. 6 is the anterior ocular segment displayed area 507 described above with reference to FIG. 5. Double-dot dashed lines 607 and 608 intersect each other at an intersection 602. The intersection 602 indicates a center of the anterior ocular segment displayed area 507. An X-Y coordinate system 601 corresponds to the coordinate system 104 illustrated in FIGS. 1A and 1B. The anterior ocular segment displayed area 507 can be divided by the double-dot dashed lines 607 and 608 into areas 603, 604, 605, and 606. When the intersection 602 is an origin of the X-Y coordinate system, the area 603 is an area of X>0 and Y>0. When the area 603 is clicked, the optical head portion 105 moves in the positive direction of the X axis and in the positive direction of the Y axis by a predetermined distance. The area 604 is an area of X>0 and Y<0. When the area 604 is clicked, the optical head portion 105 moves in the positive direction of the X axis and in the negative direction of the Y axis by a predetermined distance. The area 605 is an area of X<0 and Y<0. When the area 605 is clicked, the optical head portion 105 moves in the negative direction of the X axis and in the negative direction of the Y axis by a predetermined distance. The area 606 is an area of X<0 and Y>0. When the area 606 is clicked, the optical head portion 105 moves in the negative direction of the X axis and in the positive direction of the Y axis by a predetermined distance. When the area of X>0 on the double-dot dashed line 608 is clicked, the optical head portion 105 moves in the positive direction of the X axis by a predetermined distance. When the area of X<0 on the double-dot dashed line 608 is clicked, the optical head portion 105 moves in the negative direction of the X axis by a predetermined distance. When the area of Y>0 on the double-dot dashed line 607 is clicked, the optical head portion 105 moves in the positive direction of the Y axis by a predetermined distance. When the area of Y<0 on the double-dot dashed line 607 is clicked, the optical head portion 105 moves in the negative direction of the Y axis by a predetermined distance.

A button 506 is provided for moving the optical head portion 105 in the positive direction of the Z axis. A button 505 is provided for moving the optical head portion 105 in the negative direction of the Z axis.

A displayed area 504 displays the fundus portion of the eye to be inspected (not shown). A tomographic image on a tomographic line 511 is displayed on a displayed area 508. The displayed area 508 displays the tomographic image taken along the line (cross section) 511 of the eye to be inspected (not shown). When a record button 509 is depressed, data of the eye to be inspected is saved in a storage device (not shown). Operation flows and the like of the chin rest portion 107 and the XYZ unit 108 are described later.

In the PC 156, an operating software (OS) (not shown) is installed. There is also installed the GUI app (described above with reference to FIG. 5) for the examiner to operate the ophthalmologic apparatus. Using the GUI app, the ophthalmologic apparatus is operated so as to acquire data of the anterior ocular image, the fundus image, and the tomographic image of the eye to be inspected, etc. Further, electronic data obtained by the above-mentioned operation is image-processed and is displayed on the display 160.

A CPU unit 158 of the PC 156 controls image processing of data received from the camera link board 157, processing of the GUI app for photographing the eye to be inspected, driving of the XYZ unit 108 by the GUI app, driving of an optical unit portion (not shown) inside the head unit 105, a GUI display on the display 160, and the like.

The display 160 displays a GUI for the examiner to operate the ophthalmologic apparatus.

The mouse 162 is connected to the PC 156. A keyboard 163 is connected to the PC 156. An AC inlet connector 164 of the PC 156 is connected to an AC cable 165 described later. The AC cable 165 is used for supplying power to the AC inlet portion.

The chin rest unit portion 107 defines a height of the eye to be inspected in accordance with a command from the PC 156. The chin rest unit portion 107 is a mechanical portion for receiving the chin of the subject (not shown) so as to adjust a height of the eye. A feed screw 113 has a pitch of 2 mm. A stepping motor 112 has a specification of rotating 1.8 degrees per step pulse in a clockwise (CW) direction and in a counterclockwise (CCW) direction. The feed screw 113 is coupled to the stepping motor 112. A pin 115 is parallel to the Y axis. As to the chin rest unit portion 107, the feed screw 113 engages with a female thread (not shown) of a chin rest part 114, and the chin rest part 114 does not rotate because of the pin 115. Therefore, when the feed screw 113 is rotated by the stepping motor 112 for driving, the chin rest part 114 moves up and down so that a height of the eye to be inspected can be adjusted. Here, when a CW direction step pulse is supplied to the stepping motor 112, the chin rest part 114 moves in the negative direction of the Y axis. When a CCW direction step pulse is supplied, the chin rest part 114 moves in the positive direction of the Y axis. A stroke of the chin rest part is 60 mm. A capacitive distance sensor 164 responds when the chin rest part 114 approaches to a predetermined distance. The position at which the sensor responds becomes the origin. In addition, this position is a position of the chin rest part for packing the ophthalmologic apparatus. In other words, a position for packing of the chin rest unit portion 107 is a low end position in a drive stroke and corresponds to an origin position of the chin rest unit portion 107. A detailed flow is described later with reference to FIG. 7. The structure functions as a chin rest unit drive portion for driving the chin rest unit portion 107 in the present invention.

The XYZ unit 108 disposed on the base unit portion 106 is used for positioning the optical head portion 105 in the X, Y, and Z directions, and corresponds to an optical head unit drive portion in the present invention. The XYZ unit 108 is constituted of an X axis unit 111, a Z axis unit 110, and a Y axis unit 109.

The X axis unit 111 is constituted of a motor 116, a coupling 120, a feed screw 117, a rotation stop pin 119, an X axis base 121, and a position sensor 122. A stroke of the X axis unit 111 is 100 mm. The motor 116 is a stepping motor. The motor 116 rotates 1.8 degrees per step pulse. The feed screw 117 is mounted to a shaft of the motor 116 via the coupling 120. The feed screw 117 has a thread having a pitch of 2 mm formed thereon and engages with a female thread coupled to a Z axis base 128. The rotation stop pin 119 is a pin that prevents the Z axis base 128 from rotating. The position sensor 122 is a sensor for calibrating between a pulse count position and a physical position of the motor 116. The X axis base 121 is fixed to a base unit portion 106 with a screw. Further, the X axis base 121 holds the motor 116, the feed screw 117, and the rotation stop pin 119, and supports the Z axis unit 110 and the Y axis unit 109.

The Z axis unit 110 is constituted of a motor 123, a coupling 124, a feed screw 125, a rotation stop pin 127, a Y axis base 128, and a position sensor 126. A stroke of the Z axis unit 110 is 40 mm. The motor 123 is a stepping motor. The motor 123 rotates 1.8 degrees per step pulse. The feed screw 125 is mounted to a shaft of the motor 123 via the coupling 124. The feed screw 125 has a thread having a pitch of 2 mm formed thereon and engages with a female thread coupled to a Y axis base 133. The rotation stop pin 127 is a pin that prevents the Y axis base 133 from rotating. The position sensor 126 is a sensor for calibrating between a pulse count position and a physical position of the motor 123. The Z axis base 128 is engaged with the feed screw 117 of the X axis unit. Further, the Y axis base 128 holds the motor 123, the feed screw 125, and the rotation stop pin 127, and supports the Y axis unit 109.

The Y axis unit 109 is constituted of a motor 129, a spur gear 130, a spur gear 131, a feed screw 134, a rotation stop pin 132, and a Y axis base 133. A stroke of the Y axis unit 109 is 30 mm. Further, a direction of the stroke is parallel to the direction of gravity. The motor 129 is a stepping motor. The motor 129 rotates 1.8 degrees per step pulse. The spur gear 130 is mounted to a shaft of the motor 129. The feed screw 134 has a thread having a pitch of 2 mm formed thereon and engages with a female thread 136 coupled to the head portion. The rotation stop pin 132 is a pin for preventing the female thread 136 coupled to the head portion from rotating. The spur gear 131 is also mounted to the feed screw 134. A gear ratio between the spur gear 130 of the motor 129 and the spur gear 131 of the feed screw 134 (spur gear 131/spur gear 130) is 1.5/1. This is for reducing speed, because a weight of the optical head portion 105 is applied to the Y axis. A position sensor 135 is a sensor for calibrating between a pulse count position and a physical position of the motor 129.

Figure 3:
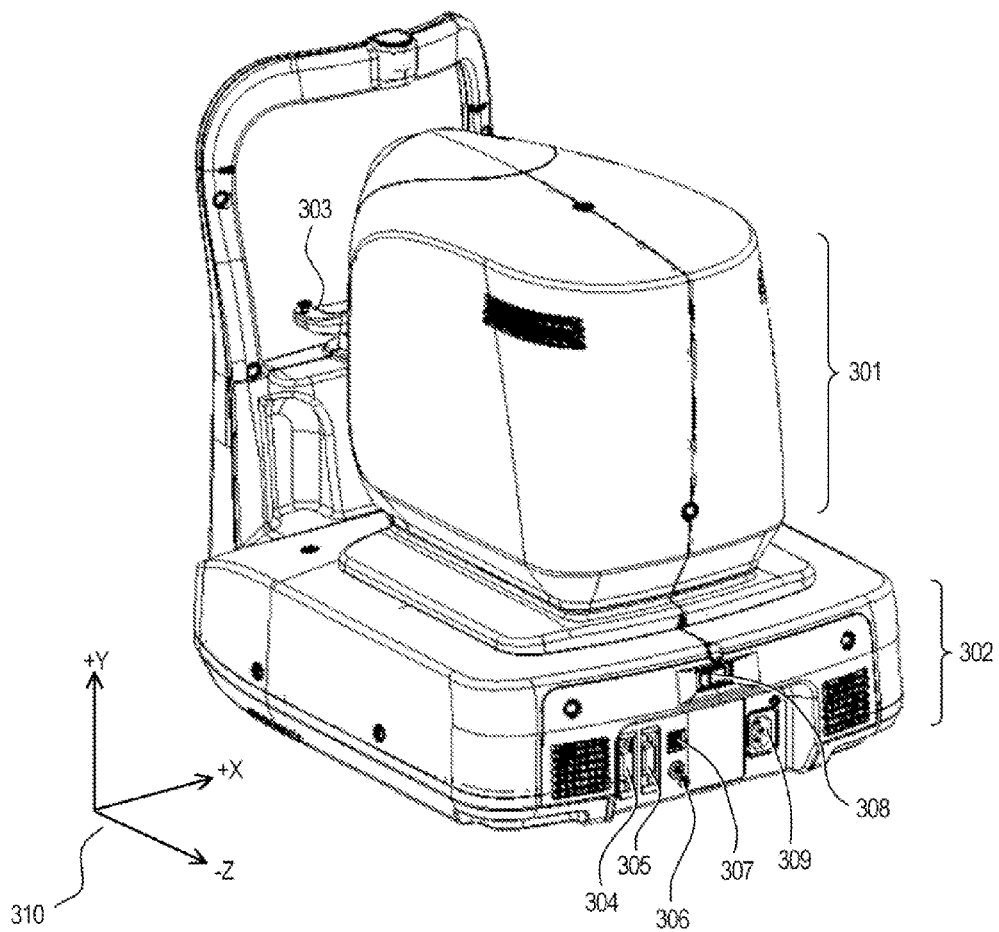
FIG. 3 is a perspective view of an external appearance of the ophthalmologic apparatus according to the first embodiment.

Next, a relationship between an actual outside appearance and the block diagrams of FIGS. 1A, 1B and 2 is described. FIG. 3 is an outside appearance perspective view of the ophthalmologic apparatus of this embodiment. An optical head portion 301 corresponds to reference numeral 105 in FIGS. 1A and 1B. A base unit portion 302 corresponds to reference numeral 106 in FIGS. 1A and 1B. A chin rest unit portion 303 corresponds to reference numeral 107 in FIGS. 1A and 1B. Camera link connectors 304 and 305 correspond to numerals 146 and 147 in FIGS. 1A and 1B. A camera link synchronization connector 306 corresponds to reference numeral 147 in FIGS. 1A and 1B. A USB connector 307 corresponds to reference numeral 151 in FIGS. 1A and 1B. An AC inlet connector 309 corresponds to reference numeral 148 in FIGS. 1A and 1B. A coordinate system 310 corresponds to numerals 102 and 104 in FIGS. 1A and 1B.

Figure 4:
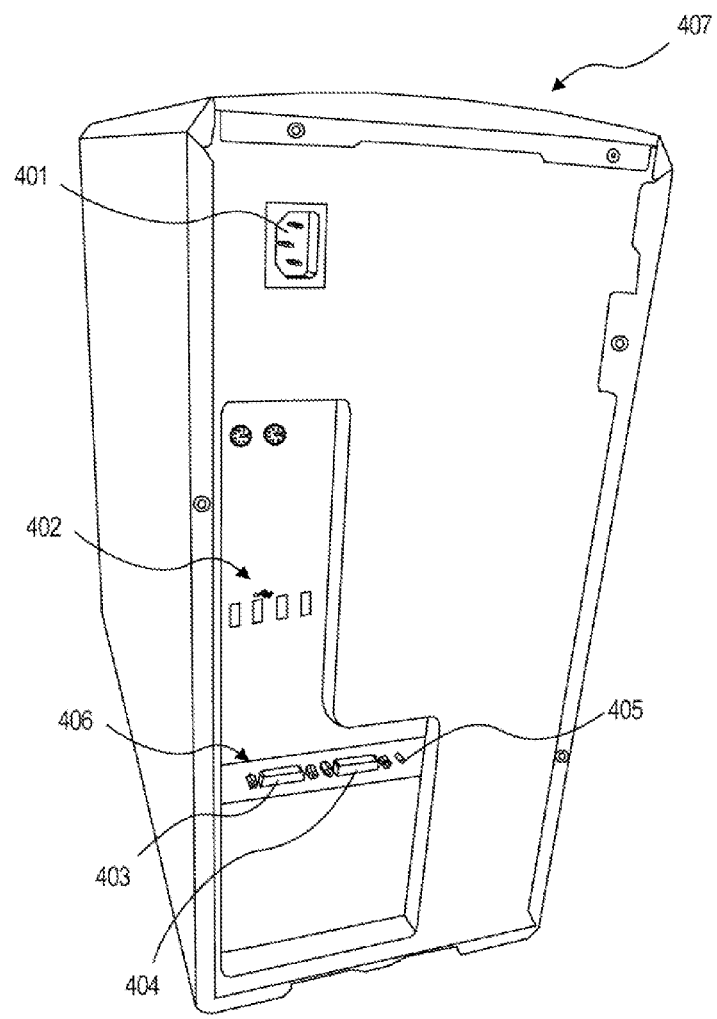
FIG. 4 is a perspective view of the PC for control according to the first embodiment.

FIG. 4 is a perspective view of the PC of this embodiment, which corresponds to the PC 156 in FIG. 2. An AC inlet 401 corresponds to reference numeral 165. A USB port 402 corresponds to reference numeral 161. A camera link board 406 corresponds to reference numeral 157. Camera link connectors 403 and 404 correspond to numerals 157(a) and 157(b). A camera link synchronization connector 405 corresponds to a camera link synchronization connector 157(c).

Operation flows of the chin rest unit portion 107 and the XYZ unit 108 are described below.

Figure 7:
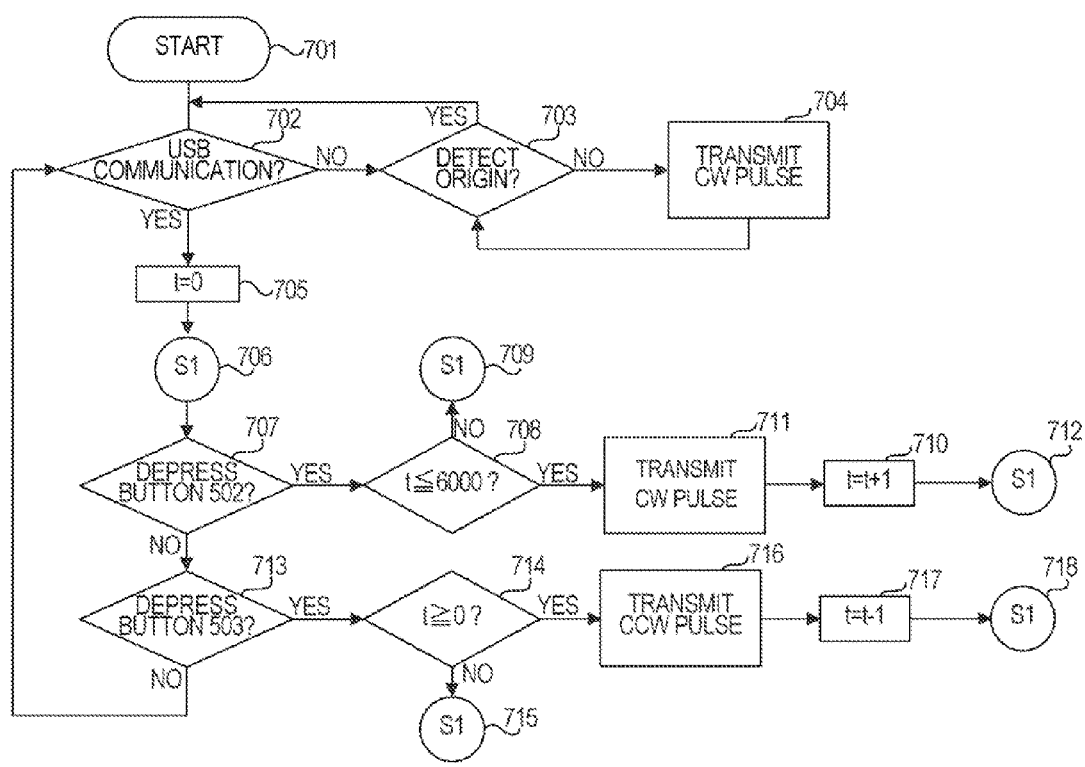
FIG. 7 is a flowchart for performing operation of a chin rest unit portion.
Figure 8:
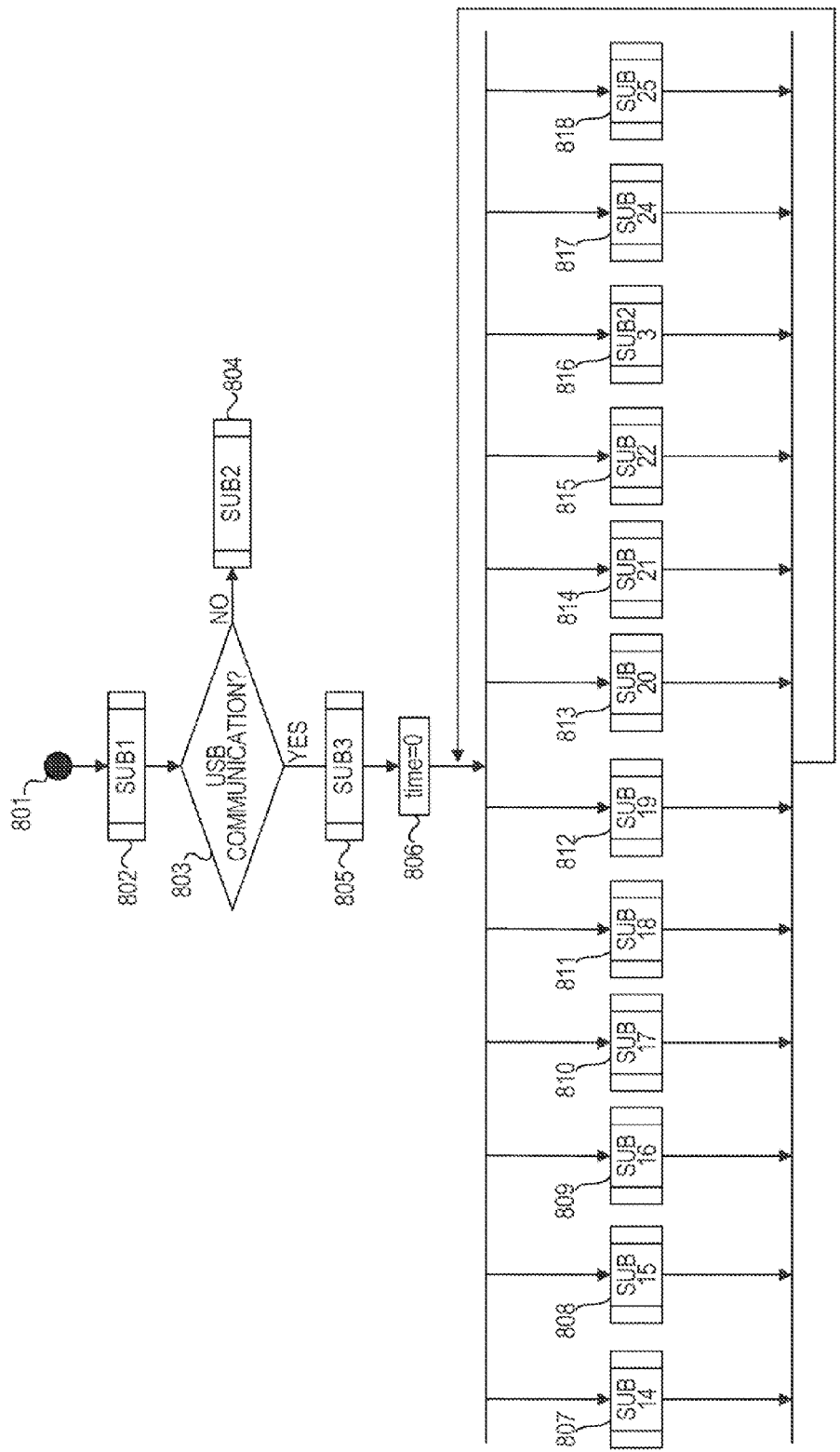
FIG. 8 is an activity diagram illustrating an operation of an XYZ unit.

First, an operation flow of the chin rest unit portion 107 is described with reference to a flowchart illustrated in FIG. 7. Step 701 is start of the flow. Step 702 is a determination section for determining whether or not USB communication is established between the PC 156 and the ophthalmologic apparatus of FIGS. 1A and 1B. If the USB communication is not established, the process proceeds to the flow of Step 703 and subsequent steps. If the USB communication is established, the process proceeds to Step 705 and subsequent steps. First, the case where the USB communication is not established is described. Step 703 is a determination section for determining whether or not a position of the chin rest part 114 is at the origin. If the chin rest part 114 is close to the distance sensor 164 by a predetermined distance so that the distance sensor 164 responds, it is determined that the chin rest part 114 is positioned at the origin, and the process proceeds to Step 702. If the distance sensor 164 does not respond, the process proceeds to Step 704. In Step 704, one CW pulse is sent to the stepping motor 112. Then, the process proceeds to Step 703. Step 703 and Step 704 are repeated until the chin rest part 114 moves to the origin position. Next, if the USB communication is established, the process proceeds to Step 705. In Step 705, a counter variable is initialized to be zero. Then, the process proceeds to next Step 706. The counter variable counts pulses sent to the stepping motor 112. Based on a value of the counter variable, a position of the chin rest can be known. Step 706 is a link point S1 of the flow. Next Step 707 is a determination section for determining whether or not a button 502 of the GUI described above with reference to FIG. 5 is clicked. If the button 502 is depressed, the process proceeds to Step 708 and subsequent steps. If the button 502 is not depressed, the process proceeds to Step 713. First, the case where the button 502 is depressed is described. In Step 708, it is determined whether or not the counter variable is smaller than 6000, that is, is smaller than a stroke upper limit value of the chin rest portion 107. If the result is false, the process proceeds to the link point S1. If the counter variable is smaller than 6000, that is, is smaller than a stroke upper limit value of the chin rest portion 107, the process proceeds to Step 710. In Step 710, one CCW pulse is sent to the stepping motor 112. Then, the process proceeds to next Step 711. In Step 711, one is added to the counter variable t. Then, the process proceeds to next Step 712. In Step 712, the process proceeds to the link point S1. Next, if the button 502 is not depressed, the process proceeds to Step 713. Step 713 is a determination section for determining whether or not the button 503 is depressed. If the button 503 is depressed, the process proceeds to Step 714. If the button 503 is not depressed, the process returns to Step 702. Because Step 702 and subsequent steps are already described, Step 714 and subsequent steps in the case where the button 503 is depressed are described. Step 714 is a determination section for determining whether or not the counter variable t is larger than zero. If the counter variable t is zero, that is, if the chin rest part 114 is positioned at the origin and is not lowered any more, the process proceeds to Step 715. Step 715 is a link point S1. If the counter variable t is larger than zero, the process proceeds to Step 716. In Step 716, one CW pulse is sent to the stepping motor 112. Then, the process proceeds to next Step 717. In Step 717, one is subtracted from the counter variable t. Then, the process proceeds to next Step 718. Step 718 is the link point S1. As described above, if the ophthalmologic apparatus of FIGS. 1A and 1B does not establish the USB communication with the PC 156, the chin rest part 114 is automatically positioned at the position for packing. Examples of scenes where the chin rest part 114 is automatically positioned at the position for packing are as follows.

1. When the USB connector cable 155 is detached from the ophthalmologic apparatus of FIGS. 1A and 1B, the chin rest part 114 is automatically positioned at the position for packing.

2. When the power switch of the ophthalmologic apparatus of FIGS. 1A and 1B is changed from an OFF state to an ON state without connecting the USB connector cable 155 of the PC 156 to the ophthalmologic apparatus of FIGS. 1A and 1B, the chin rest part 114 is automatically positioned at the position for packing.

Next, an operation flow of the XYZ unit 108 is described. Because the axes are operating in parallel, the operation is described with reference to activity diagrams. FIGS. 8 to 32 are activity diagrams illustrating the operation of the XYZ unit 108. Step 801 is an initial state of the activity. In Step 802, the process jumps to a predefined process SUB1. The predefined process SUB1 is a process in which the calibration operation of the origin of the X, Y, and Z axes is defined. Details are described later. Step 803 is a determination section for determining whether or not the USB communication between the ophthalmologic apparatus and the PC 156 is established.

If the USB communication is not established, the process jumps to a predefined process SUB2. The predefined process SUB2 is an activity for lowering the optical head portion 105 of the ophthalmologic apparatus of FIGS. 1A and 1B to the stroke limit in the negative direction of the Y axis, and positioning the optical head portion 105 at the center of the stroke in the X axis direction and in the Z axis direction. This position is a position for packing the ophthalmologic apparatus of FIGS. 1A and 1B, that is, a packing position corresponding to a first position of the present invention. Details are described later.

If the USB communication is established, the process proceeds to Step 805. In Step 805, the process jumps to a predefined process SUB3. The predefined process SUB3 is an activity for positioning the optical head portion 105 of the ophthalmologic apparatus of FIGS. 1A and 1B to 17.5 mm from the X axis origin in the X axis direction, to the center of the stroke in the Y axis direction, and to the stroke limit in the negative direction of the Z axis. This position corresponds to a position of a right eye to be inspected. Details are described later. After this process, the process proceeds to Step 806.

In Step 806, 0 (zero) is set to a time counter. Then, the process proceeds to the next parallel processing step. Twelve predefined processes are processed in parallel. Here, a general operation of the predefined process is described, and detailed activity is described later.

In Step 807, the process jumps to a predefined process SUB14. The predefined process SUB14 is a process when the area 603 of the GUI illustrated in FIG. 6 is depressed by the cursor. The optical head portion 105 moves to the positive direction both in the X axis direction and in the Y axis direction.

In Step 808, the process jumps to a predefined process SUB15. The predefined process SUB15 is a process when the area 604 of the GUI illustrated in FIG. 6 is depressed by the cursor. The optical head portion 105 moves to the positive direction in the X axis direction and to the negative direction in the Y axis direction.

In Step 809, the process jumps to a predefined process SUB16. The predefined process SUB16 is a process when the area 605 of the GUI illustrated in FIG. 6 is depressed by the cursor. The optical head portion 105 moves to the negative direction both in the X axis direction and in the Y axis direction.

In Step 810, the process jumps to a predefined process SUB17. The predefined process SUB17 is a process when the area 606 of the GUI illustrated in FIG. 6 is depressed by the cursor. The optical head portion 105 moves to the negative direction in the X axis direction and to the positive direction in the Y axis direction.

In Step 813, the process jumps to a predefined process SUB20. The predefined process SUB20 is a process when the area of X>0 on the double-dot dashed line 608 of the GUI illustrated in FIG. 6 is depressed by the cursor. The optical head portion 105 moves to the positive direction in the X axis direction.

In Step 814, the process jumps to a predefined process SUB21. The predefined process SUB21 is a process when the area of X<0 on the double-dot dashed line 608 of the GUI illustrated in FIG. 6 is depressed by the cursor. The optical head portion 105 moves to the negative direction in the X axis direction.

In Step 815, the process jumps to a predefined process SUB22. The predefined process SUB22 is a process when the area of Y>0 on the double-dot dashed line 607 of the GUI illustrated in FIG. 6 is depressed by the cursor. The optical head portion 105 moves to the positive direction in the Y axis direction.

In Step 816, the process jumps to a predefined process SUB23. The predefined process SUB23 is a process when the area of Y<0 on the double-dot dashed line 607 of the GUI illustrated in FIG. 6 is depressed by the cursor. The optical head portion 105 moves to the negative direction in the Y axis direction.

In Step 811, the process jumps to a predefined process SUB18. The predefined process SUB18 is a process when the button 506 of the GUI illustrated in FIG. 5 is depressed by the cursor. The optical head portion 105 moves to the positive direction in the Z axis direction.

In Step 812, the process jumps to a predefined process SUB19. The predefined process SUB19 is a process when the button 505 of the GUI illustrated in FIG. 5 is depressed by the cursor. The optical head portion 105 moves to the negative direction in the Z axis direction.

In Step 817, the process jumps to a predefined process SUB24. In the predefined process SUB24, the time counter is read. If a value of the time counter is smaller than 300 seconds, no operation is performed. If a value of the time counter is 300 seconds or larger, the process jumps to the predefined process SUB2, in which the optical head portion 105 of the ophthalmologic apparatus of FIGS. 1A and 1B is lowered to the stroke limit in the negative direction of the Y axis, so as to position the optical head portion 105 at the center of the stroke in the X axis direction and in the Z axis direction. This is the attitude for waiting packing as described above. Details are described later.

In Step 818, the process jumps to a predefined process SUB25. In the predefined process SUB24, it is determined whether or not the USB communication is established between the ophthalmologic apparatus of FIGS. 1A and 1B and the PC 156. If the USB communication is established, no operation is performed. If the USB communication is not established, the process jumps to the predefined process SUB2, so as to lower the optical head portion 105 of the ophthalmologic apparatus of FIGS. 1A and 1B to the stroke limit in the negative direction of the Y axis, and to position the optical head portion 105 at the center of the stroke in the X axis direction and in the Z axis direction. This is the attitude for waiting packing as described above. Details are described later. Step 807 to Step 818 described above are repeated in parallel until the power to the ophthalmologic apparatus is turned off.

In the following, the predefined processes of the activity diagram described above with reference to FIG. 8 are described.

Figure 9:
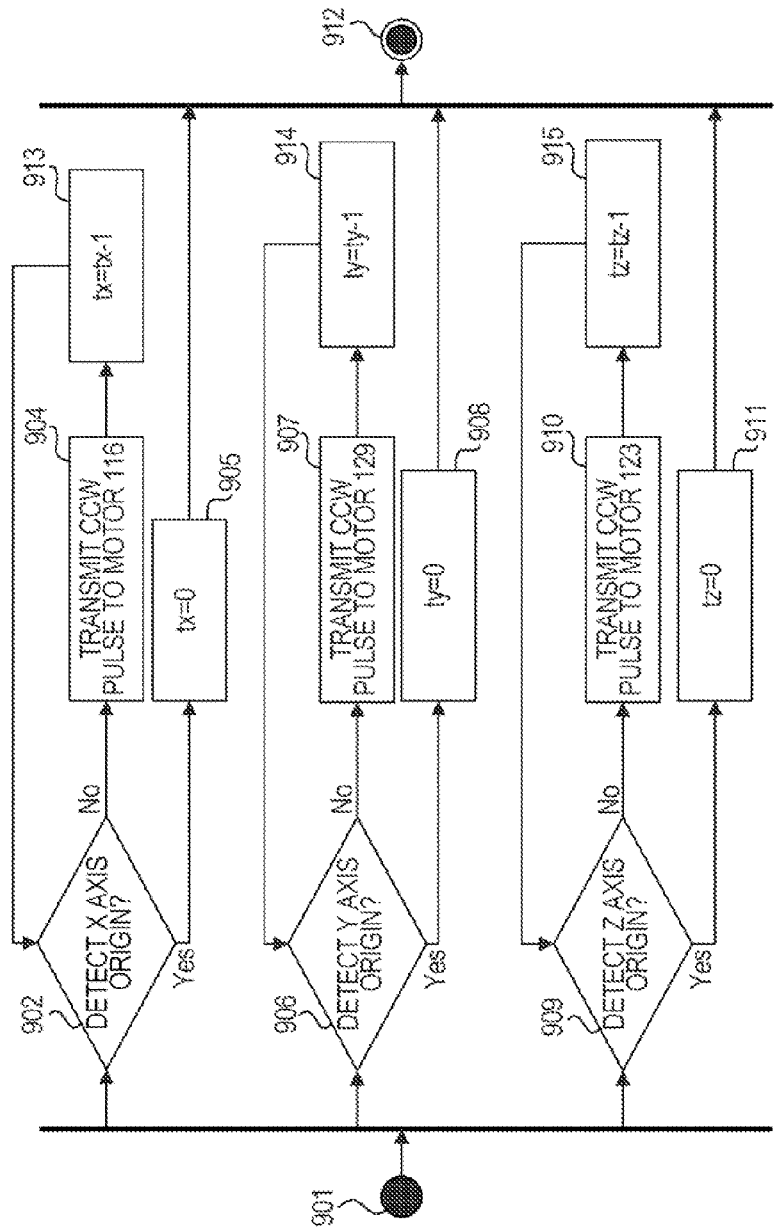
FIG. 9 is an activity diagram illustrating an operation of a predefined process SUB1.

FIG. 9 illustrates the predefined process SUB1. Step 901 is an initial state of the activity of the predefined process SUB1. After Step 901, the following three processes are processed in parallel.

Process 1. Step 902 is a determination section for determining whether or not the origin of the X axis is detected. If the origin of the X axis is detected, the process proceeds to Step 905. In Step 905, tx is set to zero. Next, the process proceeds to Step 912 that is a state where the activity of the predefined process SUB1 is finished. If the origin of the X axis is not detected, the process proceeds to Step 904 so as to send the CCW pulse to the motor 116. Further, the process proceeds to next Step 913. In Step 913, one is subtracted from tx. Then, the process proceeds to next Step 902. The loop described above is repeated until tx becomes zero, that is, until reaching to the origin of the X axis.

Process 2. Step 906 is a determination section for determining whether or not the origin of the Y axis is detected. If the origin of the Y axis is detected, the process proceeds to Step 908. In Step 908, ty is set to zero. Next, the process proceeds to Step 912 that is the state where the activity of the predefined process SUB1 is finished. If the origin of the Y axis is not detected, the process proceeds to Step 907 so as to send the CCW pulse to the motor 129. Further, the process proceeds to next Step 914. In Step 914, one is subtracted from ty. Then, the process proceeds to next Step 906. The loop described above is repeated until ty becomes zero, that is, until reaching to the origin of the Y axis.

Process 3. Step 909 is a determination section for determining whether or not the origin of the Z axis is detected. If the origin of the Z axis is detected, the process proceeds to Step 911. In Step 911, tz is set to zero. Next, the process proceeds to Step 912 that is the state where the activity of the predefined process SUB1 is finished. If the origin of the Z axis is not detected, the process proceeds to Step 910 so as to send the CCW pulse to the motor 123. Further, the process proceeds to next Step 915. In Step 915, one is subtracted from tz. Then, the process proceeds to next Step 909. The loop described above is repeated until tz becomes zero, that is, until reaching to the origin of the Z axis.

Figure 10:
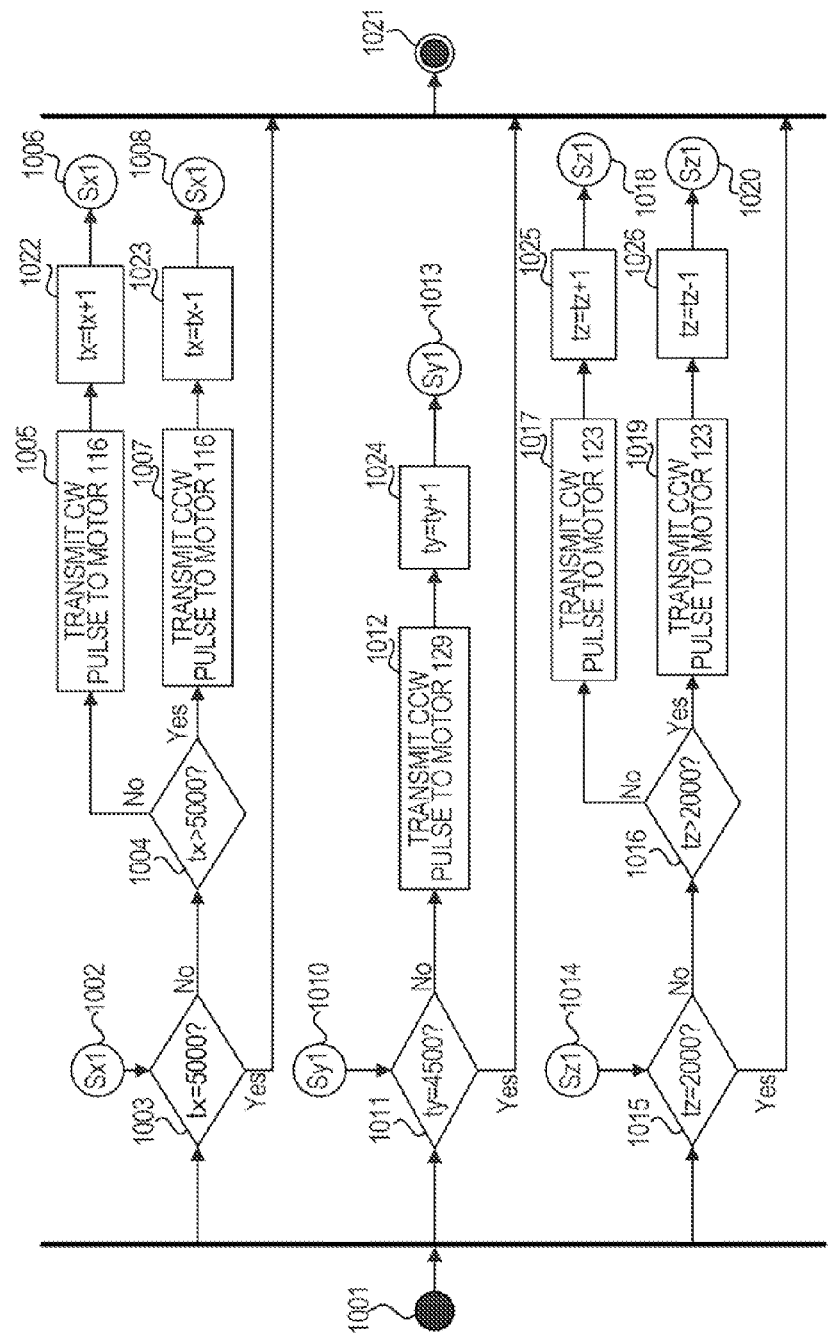
FIG. 10 is an activity diagram illustrating an operation of a predefined process SUB2.

FIG. 10 illustrates the predefined process SUB2. As described above, this predefined process is a process for changing to the attitude of the optical head portion 105 for packing. Step 1001 is an initial state of the activity of the predefined process SUB2. After Step 1001, the following three processes are processed in parallel.

Process 1. Step 1003 is a determination section for determining whether or not the optical head portion 105 is positioned at the center of the stroke in the X axis direction. If the optical head portion 105 is positioned at the center of the stroke in the X axis direction, the process proceeds to Step 1021 that is a state where the activity of the predefined process SUB2 is finished. If the optical head portion 105 is not positioned at the center of the stroke in the X axis direction, the process proceeds to Step 1004. Step 1004 is a determination section for determining whether or not tx is larger than 5,000. In other words, Step 1004 is a processing section for determining whether or not the optical head portion 105 is closer to the origin sensor 122 than the center of the stroke. If tx is larger than 5,000, the process proceeds to Step 1007. In Step 1007, the CCW pulse is sent to the motor 116. Then, the process proceeds to next Step 1023. In Step 1023, one is subtracted from tx. Then, the process proceeds to next Step 1008. Step 1008 is a link pointer Sx1, and the process jumps to a link pointer Sx1 of Step 1002. The link pointer Sx1 of Step 1002 is connected to Step 1003. If tx is smaller than 5,000, the process proceeds to Step 1005. In Step 1005, the CW pulse is sent to the motor 116. Then, the process proceeds to next Step 1022. In Step 1022, one is added to tx. Then, the process proceeds to next Step 1006. Step 1006 is a link pointer, and the process jumps to the link point Sx1 of Step 1002. The link pointer Sx1 is connected to Step 1003. As described above, Process 1 is a process for positioning the optical head portion 105 at the center of the stroke in the X axis direction.

Process 2. Step 1011 is a determination section for determining whether or not the optical head portion 105 is positioned at the stroke limit position in the negative direction of the Y axis. If the optical head portion 105 is positioned at the stroke limit position in the negative direction of the Y axis, the process proceeds to Step 1021 that is a state where the activity of the predefined process SUB2 is finished. If the optical head portion 105 is not positioned at the stroke limit position in the negative direction of the Y axis, the process proceeds to Step 1012. In Step 1012, the CW pulse is sent to the motor 129. Then, the process proceeds to next Step 1024. In Step 1024, one is added to ty. Then, the process proceeds to next Step 1013. Step 1013 is a link pointer Sy1, and the process jumps to a link pointer Sy1 of Step 1010. The link pointer Sy1 of Step 1010 is connected to Step 1011. As described above, Process 2 is a process for positioning the optical head portion 105 at the stroke limit position in the negative direction of the Y axis.

Process 3. Step 1015 is a determination section for determining whether or not the optical head portion 105 is positioned at the center of the stroke in the Z axis direction. If the optical head portion 105 is positioned at the center of the stroke in the Z axis direction, the process proceeds to Step 1021 that is the state where the activity of the predefined process SUB2 is finished. If the optical head portion 105 is not positioned at the center of the stroke in the Z axis direction, the process proceeds to Step 1016. Step 1016 is a determination section for determining whether or not tz is larger than 2,000. In other words, Step 1016 is a processing section for determining whether or not the optical head portion 105 is closer to the origin sensor 126 than the center of the stroke. If tz is larger than 2,000, the process proceeds to Step 1019. In Step 1019, the CCW pulse is sent to the motor 123. Then, the process proceeds to next Step 1026. In Step 1026, one is subtracted from tz. Then, the process proceeds to next Step 1020. Step 1020 is a link pointer, and the process jumps to a link pointer Sz1 of Step 1014. The link pointer Sz1 is connected to Step 1015. If tz is smaller than 2,000, the process proceeds to Step 1017. In Step 1017, the CW pulse is sent to the motor 123. Then, the process proceeds to next Step 1025. In Step 1025, one is added to tz. Then, the process proceeds to next Step 1018. Step 1018 is a link pointer, and the process jumps to the link point Sz1 of Step 1014. The link pointer Sz1 is connected to Step 1015. As described above, Process 3 is a process for positioning the optical head portion 105 at the center of the stroke in the Z axis direction.

Figure 11:
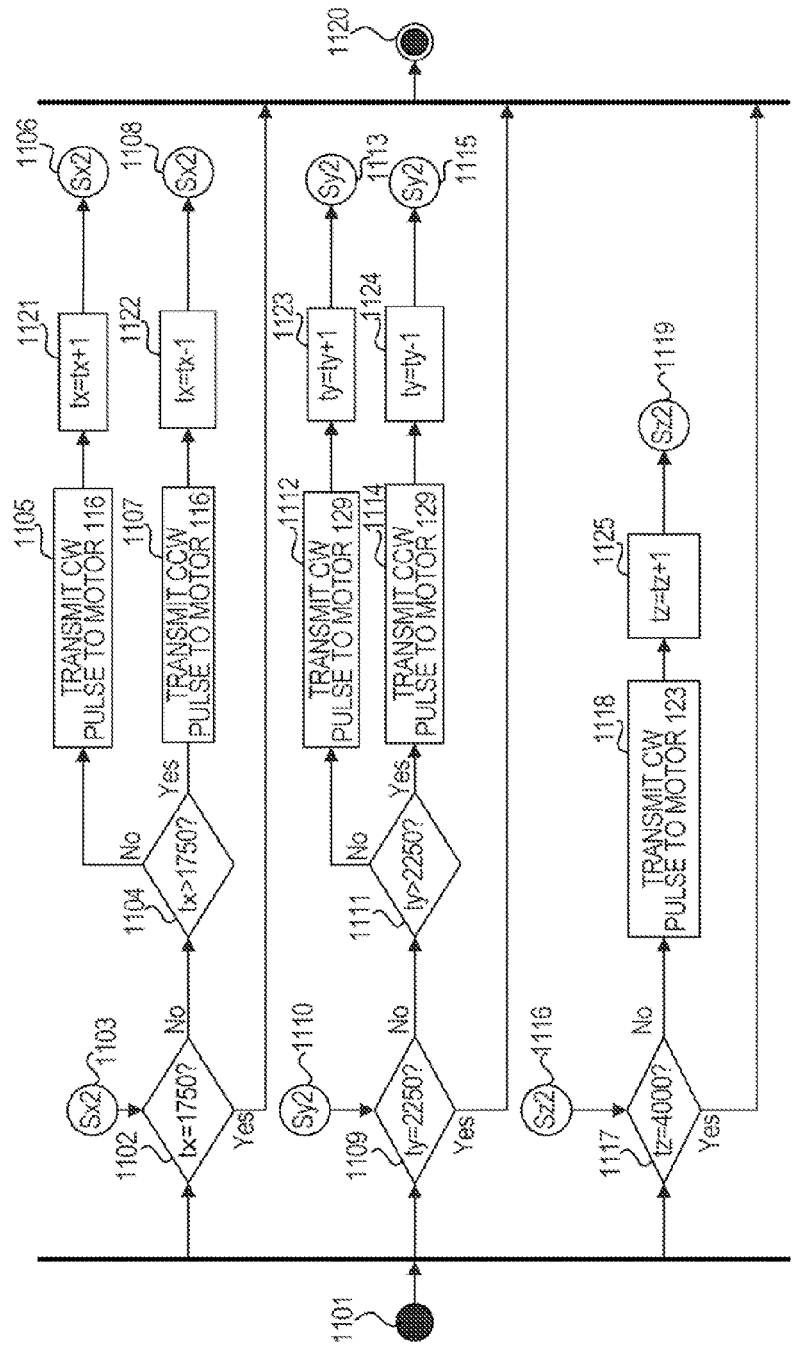
FIG. 11 is an activity diagram illustrating an operation of a predefined process SUB3.

FIG. 11 illustrates the predefined process SUB3. As described above, this predefined process is a process for changing the attitude of the optical head portion 105 to the waiting attitude for photographing a right eye to be inspected. Step 1101 is an initial state of the activity of the predefined process SUB3. After Step 1101, the following three processes are processed in parallel.

Process 1. Step 1102 is a determination section for determining whether or not a position of the optical head portion 105 in the X axis direction is at a position of 17.5 mm from the origin. If the position in the X axis direction is at a position of 17.5 mm from the origin, the process proceeds to Step 1120 that is a state where the activity of the predefined process SUB3 is finished. If the position in the X axis direction is not at the position of 17.5 mm from the origin, the process proceeds to Step 1104. Step 1104 is a determination section for determining whether or not tx is larger than 1,750. In other words, Step 1104 is a processing section for determining whether or not the optical head portion 105 is closer to the origin sensor 122 than the position of the eye to be inspected (not shown) X=17.5 mm. If tx is larger than 1,750, the process proceeds to Step 1107. In Step 1107, the CCW pulse is sent to the motor 116. Then, the process proceeds to next Step 1122. In Step 1122, one is subtracted from tx. Then, the process proceeds to next Step 1108. Step 1108 is a link pointer Sx2, and the process jumps to a link point Sx2 of Step 1103. The link pointer Sx2 of Step 1103 is connected to Step 1102. If tx is smaller than 1,750, the process proceeds to Step 1105. In Step 1105, the CW pulse is sent to the motor 116. Then, the process proceeds to next Step 1121. In Step 1121, one is added to tx. Then, the process proceeds to next Step 1106. Step 1106 is a link pointer Sx2, and the process jumps to the link pointer Sx2 of Step 1103. The link pointer Sx2 is connected to Step 1102. As described above, Process 1 is a process for positioning the optical head portion 105 right in front of the eye to be inspected (not shown) in the X axis direction.

Process 2. Step 1109 is a determination section for determining whether or not the optical head portion 105 is positioned at the center of the stroke in the Y axis direction. If the optical head portion 105 is positioned at the center of the stroke in the Y axis direction, the process proceeds to Step 1120 that is the state where the activity of the predefined process SUB3 is finished. If the optical head portion 105 is not positioned at the center of the stroke in the Y axis direction, the process proceeds to Step 1111. Step 1111 is a determination section for determining whether or not ty is larger than 2,250. If ty is larger than 2,250, the process proceeds to Step 1114. In Step 1114, the CCW pulse is sent to the motor 129. Then, the process proceeds to next Step 1124. In Step 1124, one is subtracted from ty. Then, the process proceeds to next Step 1115. Step 1115 is a link pointer Sy2, and the process jumps to the link point Sy2 of Step 1110. The link pointer Sy2 of Step 1110 is connected to Step 1109. If ty is smaller than 2,250, the process proceeds to Step 1112. In Step 1112, the CW pulse is sent to the motor 129. Then, the process proceeds to next Step 1123. In Step 1123, one is added to ty. Then, the process proceeds to next Step 1113. Step 1113 is a link pointer Sy2, and the process jumps to the link pointer Sy2 of Step 1110. The link pointer Sy2 is connected to Step 1109. As described above, Process 2 is a process for positioning the optical head portion 105 at the center of the stroke in the Y axis direction.

Process 3. Step 1117 is a determination section for determining whether or not the optical head portion 105 is positioned at the stroke limit position in the negative direction of the Z axis. If the positioning is performed at the stroke limit position in the negative direction of the Z axis, the process proceeds to Step 1120 that is the state where the activity of the predefined process SUB3 is finished. If the optical head portion 105 is not positioned at the stroke limit position in the negative direction of the Z axis, the process proceeds to Step 1118. In Step 1118, the CW pulse is sent to the motor 123. Then, the process proceeds to next Step 1125. In Step 1125, one is added to tz. Then, the process proceeds to next Step 1119. Step 1119 is a link pointer, and the process jumps to a link pointer Sz2 of Step 1116. The link pointer Sz2 of Step 1116 is connected to Step 1117. As described above, Process 3 is a process for positioning the optical head portion 105 at the stroke limit position in the negative direction of the Z axis.

Figure 22:
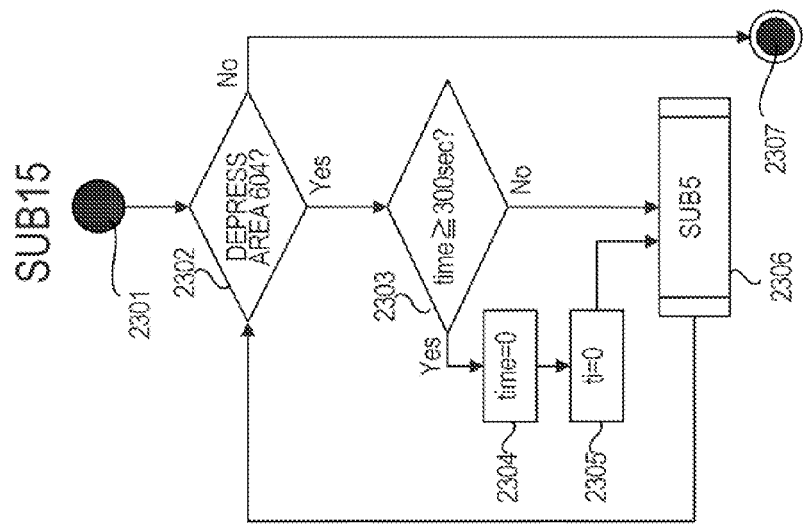
FIG. 22 is an activity diagram illustrating an operation of a predefined process SUB14.

FIG. 22 illustrates the predefined process SUB14, which defines an operation when the area 603 of the GUI illustrated in FIG. 6 is clicked by the cursor 501. Step 2201 is an initial state of the activity of the predefined process SUB14. Step 2202 is a determination section for determining whether or not the area 603 of the GUI illustrated in FIG. 6 is depressed by the cursor 501. If the area 603 is depressed, the process proceeds to Step 2203. Step 2203 is a determination section for determining whether or not a value of the timer counter is 300 seconds or larger. If the value of the timer counter is 300 seconds or larger, the process proceeds to Steps 2204, 2205, and 2206. In Step 2204, the timer counter is reset to zero. In Step 2205, ti is reset to zero. This variable ti is described later with reference to FIGS. 32 and 33. In Step 2206, a predefined process SUB4 is performed. The predefined process SUB4 is described after description of the predefined process SUB14. If the timer counter value is smaller than 300 seconds, the process proceeds to Step 2206. When the process of Step 2206 is finished, the process returns to Step 2202. If the area 603 of the GUI illustrated in FIG. 6 is not depressed by the cursor 501, the process proceeds to Step 2207. Step 2207 is a state where the activity of the predefined process SUB14 is finished.

Figure 12:
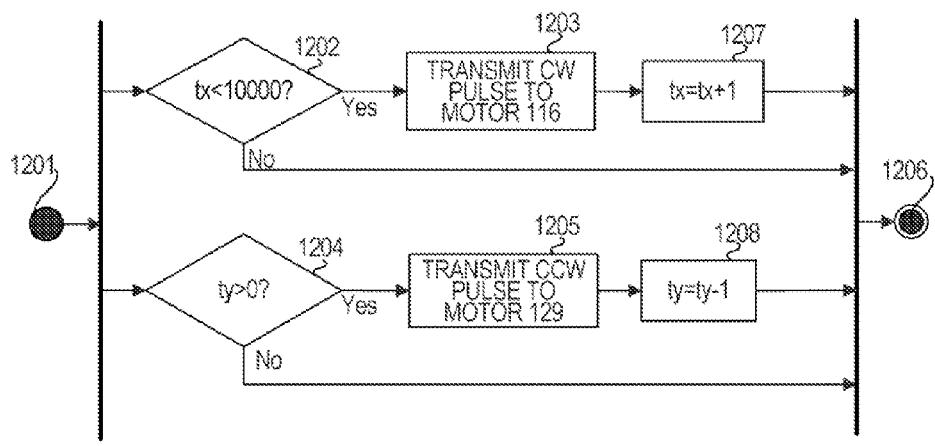
FIG. 12 is an activity diagram illustrating an operation of a predefined process SUB4.

FIG. 12 illustrates the predefined process SUB4. This predefined process is a process that is used for the predefined process SUB14 as described above. Step 1201 is an initial state of the activity of the predefined process SUB4. After Step 1201, the following two processes are processed in parallel.

Process 1. Step 1202 is a determination section for determining whether or not the position of the optical head portion 105 in the X axis direction has reached to the limit position in the positive direction. If tx is smaller than 10,000, that is, smaller than the stroke limit in the positive direction, the process proceeds to Step 1203. In Step 1203, the CW pulse is sent to the motor 116. Then, the process proceeds to next Step 1207. In Step 1207, one is added to tx. Then, the process proceeds to next Step 1206. Step 1206 is a state where the activity of the predefined process SUB4 is finished. If tx is 10,000, that is, if the optical head portion 105 has reached to the stroke limit in the positive direction, the process proceeds to Step 1206.

Process 2. Step 1204 is a determination section for determining whether or not the position of the optical head portion 105 in the Y axis direction has reached to the limit position in the positive direction. If ty is larger than zero, that is, smaller than the stroke limit in the positive direction of the Y axis, the process proceeds to Step 1205. In Step 1205, the CCW pulse is sent to the motor 129. Then, the process proceeds to next Step 1208. In Step 1208, one is subtracted from ty. Then, the process proceeds to next Step 1206. Step 1206 is the state where the activity of the predefined process SUB4 is finished. If ty is zero, that is, if the optical head portion 105 has reached to the stroke limit in the positive direction of the Y axis, the process proceeds to Step 1206.

The parallel processes described above are performed so that the process of moving the optical head portion 105 in the positive direction of the X axis and in the positive direction of the Y axis is performed.

Figure 23:
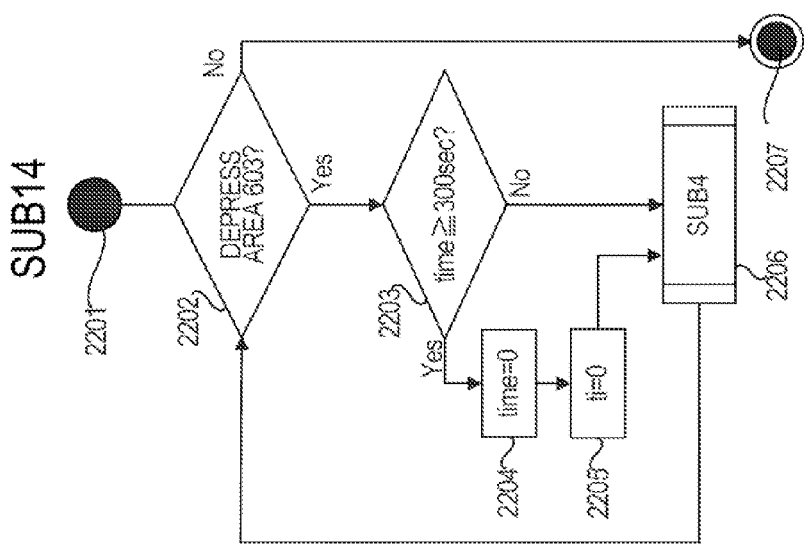
FIG. 23 is an activity diagram illustrating an operation of a predefined process SUB15.

FIG. 23 illustrates the predefined process SUB15, which defines an operation when the area 604 of the GUI illustrated in FIG. 6 is clicked by the cursor 501. Step 2301 is an initial state of the activity of the predefined process SUB15. Step 2302 is a determination section for determining whether or not the area 604 of the GUI illustrated in FIG. 6 is depressed by the cursor 501. If the area 604 is depressed, the process proceeds to Step 2303. Step 2303 is a determination section for determining whether or not a value of the timer counter is 300 seconds or larger. If the value of the timer counter is 300 seconds or larger, the process proceeds to Steps 2304, 2305 and 2306. In Step 2304, the timer counter is reset to zero. In Step 2305, ti is reset to zero. This variable ti is described later with reference to FIGS. 32 and 33. In Step 2306, a predefined process SUB5 is performed. The predefined process SUB5 is described after description of the predefined process SUB15. If the timer counter value is smaller than 300 seconds, the process proceeds to Step 2306. When the process of Step 2306 is finished, the process returns to Step 2302. If the area 604 of the GUI illustrated in FIG. 6 is not depressed by the cursor 501, the process proceeds to Step 2307. Step 2307 is a state where the activity of the predefined process SUB15 is finished.

Figure 13:
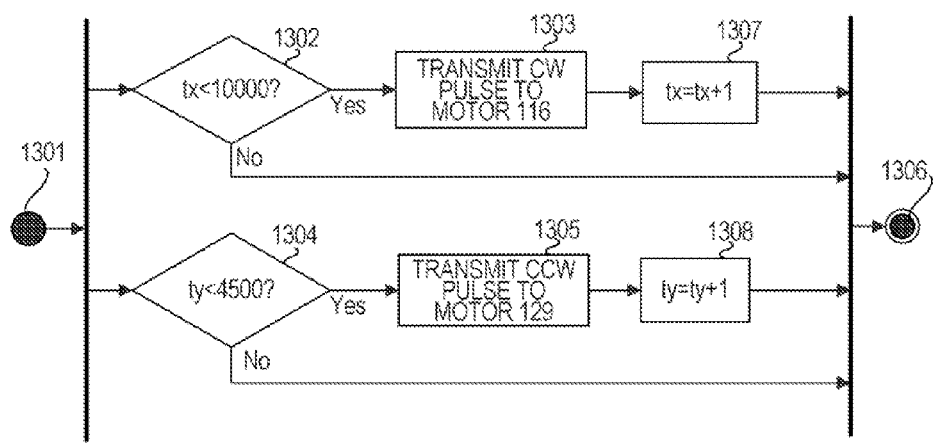
FIG. 13 is an activity diagram illustrating an operation of a predefined process SUB5.

FIG. 13 illustrates the predefined process SUB5. This predefined process is a process that is used for the predefined process SUB15 as described above. Step 1301 is an initial state of the activity of the predefined process SUB5. After Step 1301, the following two processes are processed in parallel.

Process 1. Step 1302 is a determination section for determining whether or not the position of the optical head portion 105 in the X axis direction has reached to the limit position in the positive direction. If tx is smaller than 10,000, that is, smaller than the stroke limit in the positive direction, the process proceeds to Step 1303. In Step 1303, the CW pulse is sent to the motor 116. Then, the process proceeds to next Step 1307. In Step 1307, one is added to tx. Then, the process proceeds to next Step 1306. Step 1306 is a state where the activity of the predefined process SUB5 is finished. If tx is 10,000, that is, if the optical head portion 105 has reached to the stroke limit in the positive direction, the process proceeds to Step 1306.

Process 2. Step 1304 is a determination section for determining whether or not the position of the optical head portion 105 in the Y axis direction has reached to the limit position in the negative direction. If ty is smaller than 4,500, that is, when the position of the optical head portion 105 in the Y axis direction is on the positive side with respect to the stroke limit in the negative direction, the process proceeds to Step 1305. In Step 1305, the CW pulse is sent to the motor 129. Then, the process proceeds to next Step 1308. In Step 1308, one is added to ty. Then, the process proceeds to next Step 1306. If ty is 4,500, that is, if the optical head portion 105 has reached to the stroke limit in the negative direction of the Y axis, the process proceeds to Step 1306. Step 1306 is the state where the activity of the predefined process SUB5 is finished.

The parallel processes described above are performed so that the process of moving the optical head portion 105 in the positive direction of the X axis and in the negative direction of the Y axis is performed.

Figure 24:
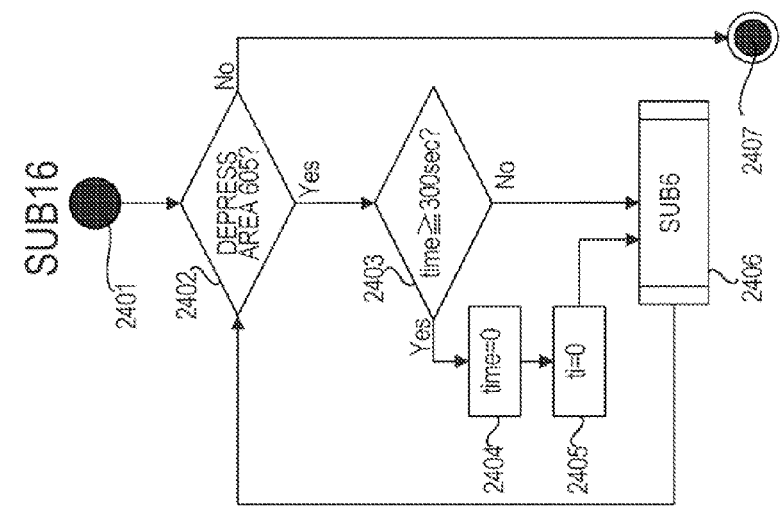
FIG. 24 is an activity diagram illustrating an operation of a predefined process SUB16.

FIG. 24 illustrates the predefined process SUB16, which defines an operation when the area 605 of the GUI illustrated in FIG. 6 is clicked by the cursor 501. Step 2401 is an initial state of the activity of the predefined process SUB16. Step 2402 is a determination section for determining whether or not the area 605 of the GUI illustrated in FIG. 6 is depressed by the cursor 501. If the area 605 is depressed, the process proceeds to Step 2403. Step 2403 is a determination section for determining whether or not a value of the timer counter is 300 seconds or larger. If the value of the timer counter is 300 seconds or larger, the process proceeds to Steps 2404, 2405 and 2406. In Step 2404, the timer counter is reset to zero. In Step 2405, ti is reset to zero. This variable ti is described later with reference to FIGS. 32 and 33. In Step 2406, a predefined process SUB6 is performed. The predefined process SUB6 is described after description of the predefined process SUB16. If the timer counter value is smaller than 300 seconds, the process proceeds to Step 2406. When the process of Step 2406 is finished, the process returns to Step 2402. If the area 605 of the GUI illustrated in FIG. 6 is not depressed by the cursor 501, the process proceeds to Step 2407. Step 2407 is a state where the activity of the predefined process SUB16 is finished.

Figure 14:
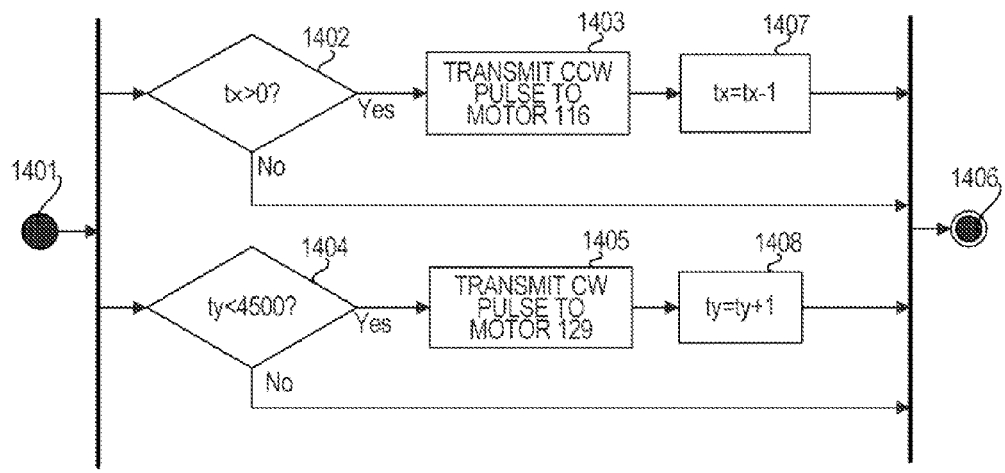
FIG. 14 is an activity diagram illustrating an operation of a predefined process SUB6.

FIG. 14 illustrates the predefined process SUB6. This predefined process is a process that is used for the predefined process SUB16 as described above. Step 1401 is an initial state of the activity of the predefined process SUB6. After that, the following two processes are processed in parallel.

Process 1. Step 1402 is a determination section for determining whether or not the position of the optical head portion 105 in the X axis direction is other than the origin. If the position of the optical head portion 105 in the X axis direction is other than the origin, the process proceeds to Step 1403. In Step 1403, the CCW pulse is sent to the motor 116. Then, the process proceeds to next Step 1407. In Step 1407, one is subtracted from tx. Then, the process proceeds to next Step 1406. If tx is zero, that is, if the position of the optical head portion 105 in the X axis direction is the origin, the process proceeds to Step 1406. Step 1406 is a state where the activity of the predefined process SUB6 is finished.

Process 2. Step 1404 is a determination section for determining whether or not the position of the optical head portion 105 in the Y axis direction has reached to the limit position in the negative direction. If ty is smaller than 4,500, that is, when the position of the optical head portion 105 in the Y axis direction is on the positive side with respect to the stroke limit in the negative direction, the process proceeds to Step 1405. In Step 1405, the CW pulse is sent to the motor 129. Then, the process proceeds to next Step 1408. In Step 1408, one is added to ty. Then, the process proceeds to next Step 1406. If ty is 4,500, that is, if the optical head portion 105 has reached to the stroke limit in the negative direction of the Y axis, the process proceeds to Step 1406. Step 1406 is the state where the activity of the predefined process SUB6 is finished.

The parallel processes described above are performed so that the process of moving the optical head portion 105 in the negative direction of the X axis and in the negative direction of the Y axis is performed.

Figure 25:
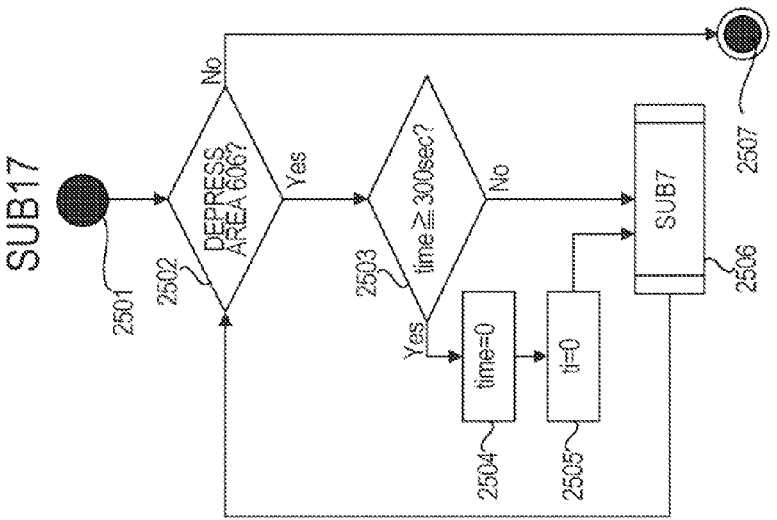
FIG. 25 is an activity diagram illustrating an operation of a predefined process SUB17.

FIG. 25 illustrates the predefined process SUB17, which defines an operation when the area 606 of the GUI illustrated in FIG. 6 is clicked by the cursor 501. Step 2501 is an initial state of the activity of the predefined process SUB17. Step 2502 is a determination section for determining whether or not the area 606 of the GUI illustrated in FIG. 6 is depressed by the cursor 501. If the area 606 is depressed, the process proceeds to Step 2503. Step 2503 is a determination section for determining whether or not a value of the timer counter is 300 seconds or larger. If the value of the timer counter is 300 seconds or larger, the process proceeds to Steps 2504, 2505, and 2506. In Step 2504, the timer counter is reset to zero. In Step 2505, ti is reset to zero. This variable ti is described later with reference to FIGS. 32 and 33. In Step 2506, a predefined process SUB7 is performed. The predefined process SUB7 is described after description of the predefined process SUB17. If the timer counter value is smaller than 300 seconds, the process proceeds to Step 2506. When the process of Step 2506 is finished, the process returns to Step 2502. If the area 606 of the GUI illustrated in FIG. 6 is not depressed by the cursor 501, the process proceeds to Step 2507. Step 2507 is a state where the activity of the predefined process SUB17 is finished.

Figure 15:
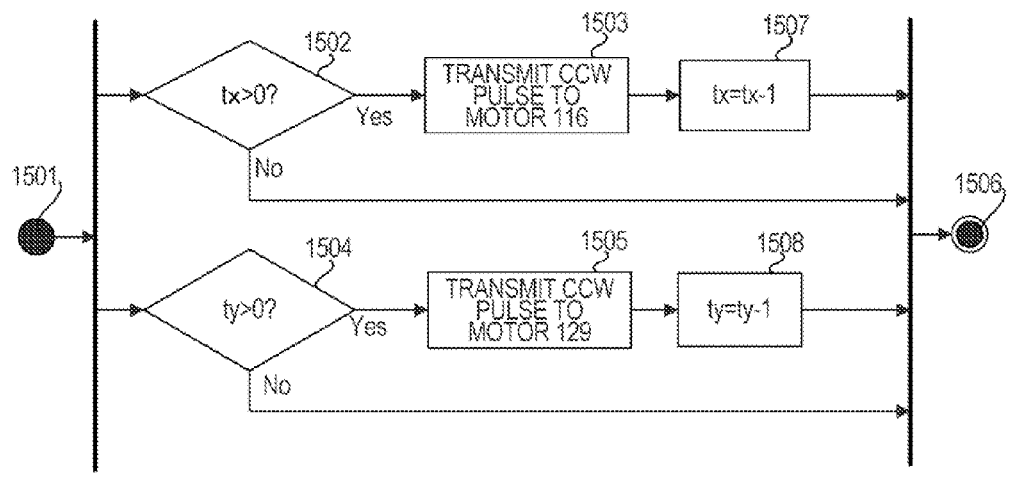
FIG. 15 is an activity diagram illustrating an operation of a predefined process SUB7.

FIG. 15 illustrates the predefined process SUB7. This predefined process is a process that is used for the predefined process SUB17 as described above. Step 1501 is an initial state of the activity of the predefined process SUB7. After Step 1501, the following two processes are processed in parallel.

Process 1. Step 1502 is a determination section for determining whether or not the position of the optical head portion 105 in the X axis direction is other than the origin. If the position of the optical head portion 105 in the X axis direction is other than the origin, the process proceeds to Step 1503. In Step 1503, the CCW pulse is sent to the motor 116. Then, the process proceeds to next Step 1507. In Step 1507, one is subtracted from tx. Then, the process proceeds to next Step 1506. If tx is zero, that is, if the position of the optical head portion 105 in the X axis direction is the origin, the process proceeds to Step 1506. Step 1506 is a state where the activity of the predefined process SUB7 is finished.

Process 2. Step 1504 is a determination section for determining whether or not the position of the optical head portion 105 in the Y axis direction is the origin. If ty is larger than 0, that is, if the position of the optical head portion 105 in the Y axis direction is other than the origin, the process proceeds to Step 1505. In Step 1505, the CCW pulse is sent to the motor 129. Then, the process proceeds to next Step 1508. In Step 1508, one is subtracted from ty. Then, the process proceeds to next Step 1506. If ty is 0, that is, if the position of the optical head portion 105 in the Y axis direction is the origin, the process proceeds to Step 1506. Step 1506 is a state where the activity of the predefined process SUB7 is finished.

The parallel processes described above are performed so that the process of moving the optical head portion 105 in the negative direction of the X axis and in the positive direction of the Y axis is performed.

Figure 26:
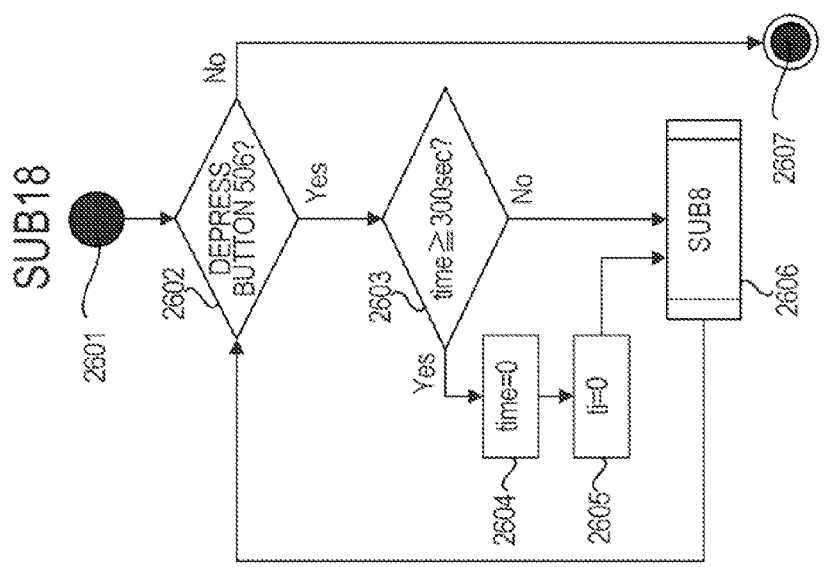
FIG. 26 is an activity diagram illustrating an operation of a predefined process SUB18.

FIG. 26 illustrates the predefined process SUB18, which defines an operation when the button 506 of the GUI illustrated in FIG. 5 is clicked by the cursor 501. Step 2601 is an initial state of the activity of the predefined process SUB18. Step 2602 is a determination section for determining whether or not the button 506 of the GUI illustrated in FIG. 5 is depressed by the cursor 501. If the button 506 is depressed, the process proceeds to Step 2603. Step 2603 is a determination section for determining whether or not a value of the timer counter is 300 seconds or larger. If the value of the timer counter is 300 seconds or larger, the process proceeds to Steps 2604, 2605, and 2606. In Step 2604, the timer counter is reset to zero. In Step 2605, ti is reset to zero. This variable ti is described later with reference to FIGS. 32 and 33. In Step 2606, a predefined process SUB8 is performed. The predefined process SUB8 is described after description of the predefined process SUB18. If the timer counter value is smaller than 300 seconds, the process proceeds to Step 2606. When the process of Step 2606 is finished, the process returns to Step 2602. If the button 506 of the GUI illustrated in FIG. 5 is not depressed by the cursor 501, the process proceeds to Step 2607. Step 2607 is a state where the activity of the predefined process SUB18 is finished.

Figure 16:
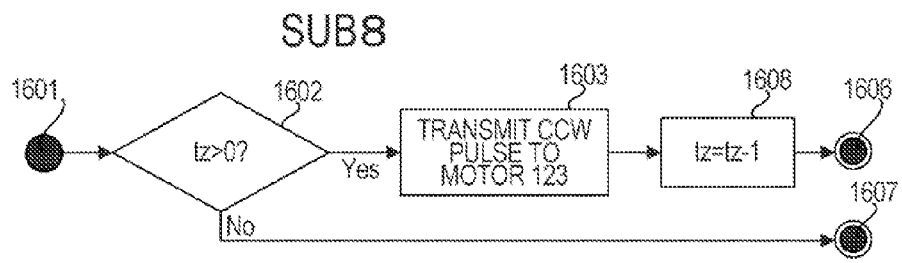
FIG. 16 is an activity diagram illustrating an operation of a predefined process SUB8.

FIG. 16 illustrates the predefined process SUB8. This predefined process is a process that is used for the predefined process SUB18 as described above. Step 1601 is an initial state of the activity of the predefined process SUB8. Step 1602 is a determination section for determining whether or not the position of the optical head portion 105 in the Z axis direction is the origin. If the position of the optical head portion 105 in the Z axis direction is other than the origin, the process proceeds to Step 1603. In Step 1603, the CCW pulse is sent to the motor 123. Then, the process proceeds to next Step 1608. In Step 1608, one is subtracted from tz. Then, the process proceeds to next Step 1606. Step 1606 is a state where the activity of the predefined process SUB8 is finished. If the position of the optical head portion 105 in the Z axis direction is the origin, the process proceeds to Step 1607. Step 1607 is a state where the activity of the predefined process SUB8 is finished.

Figure 27:
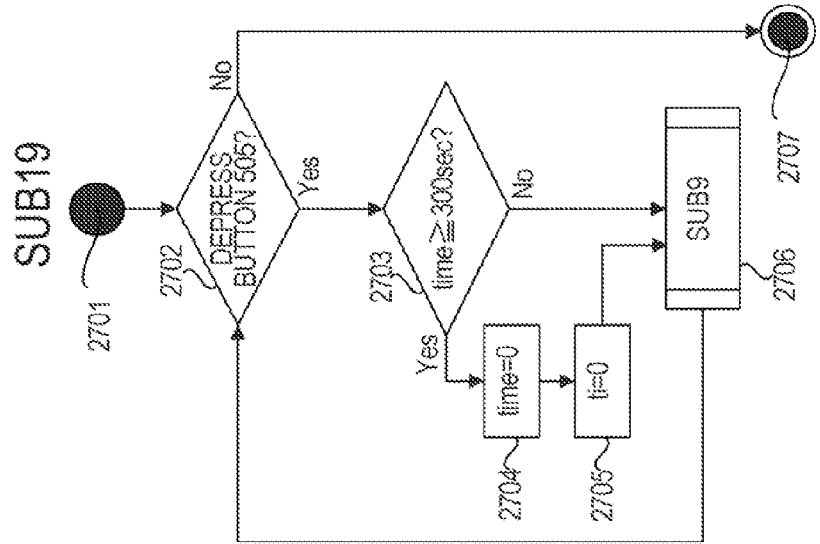
FIG. 27 is an activity diagram illustrating an operation of a predefined process SUB19.

FIG. 27 illustrates the predefined process SUB19, which defines an operation when the button 505 of the GUI illustrated in FIG. 5 is depressed by the cursor 501. Step 2701 is an initial state of the activity of the predefined process SUB19. Step 2702 is a determination section for determining whether or not the button 505 of the GUI illustrated in FIG. 5 is depressed by the cursor 501. If the button 505 is depressed, the process proceeds to Step 2703. Step 2703 is a determination section for determining whether or not a value of the timer counter is 300 seconds or larger. If the value of the timer counter is 300 seconds or larger, the process proceeds to Steps 2704, 2705, and 2706. In Step 2704, the timer counter is reset to zero. In Step 2705, ti is reset to zero. This variable ti is described later with reference to FIGS. 32 and 33. In Step 2706, a predefined process SUB9 is performed. The predefined process SUB9 is described after description of the predefined process SUB19. If the timer counter value is smaller than 300 seconds, the process proceeds to Step 2706. When the process of Step 2706 is finished, the process returns to Step 2702. If the button 505 of the GUI illustrated in FIG. 5 is not depressed by the cursor 501, the process proceeds to Step 2707. Step 2707 is a state where the activity of the predefined process SUB19 is finished.

Figure 17:
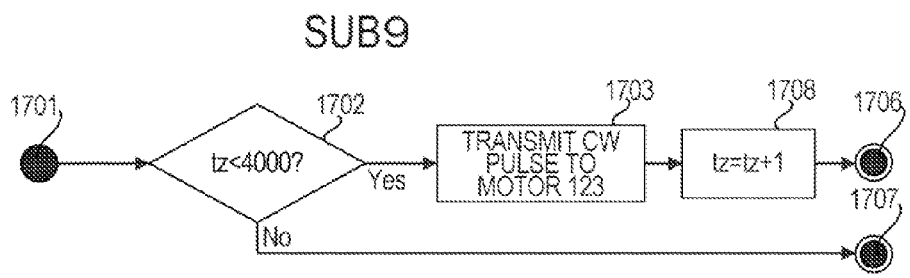
FIG. 17 is an activity diagram illustrating an operation of a predefined process SUB9.

FIG. 17 illustrates the predefined process SUB9. This predefined process is a process that is used for the predefined process SUB19 as described above. Step 1701 is an initial state of the activity of the predefined process SUB9. Step 1702 is a determination section for determining whether or not tz is smaller than 4,000, that is, whether or not the position of the optical head portion 105 is other than the stroke limit position in the negative direction of the Z axis. If the position of the optical head portion 105 in the Z axis direction is other than the stroke limit position in the negative direction of the Z axis, the process proceeds to Step 1703. In Step 1703, the CW pulse is sent to the motor 123. Then, the process proceeds to next Step 1708. In Step 1708, one is added to tz. Then, the process proceeds to next Step 1706. Step 1706 is a state where the activity of the predefined process SUB9 is finished. If tz is 4,000, that is, the optical head portion 105 is at the stroke limit position in the negative direction of the Z axis, the process proceeds to Step 1707. Step 1707 is a state where the activity of the predefined process SUB9 is finished.

Figure 28:
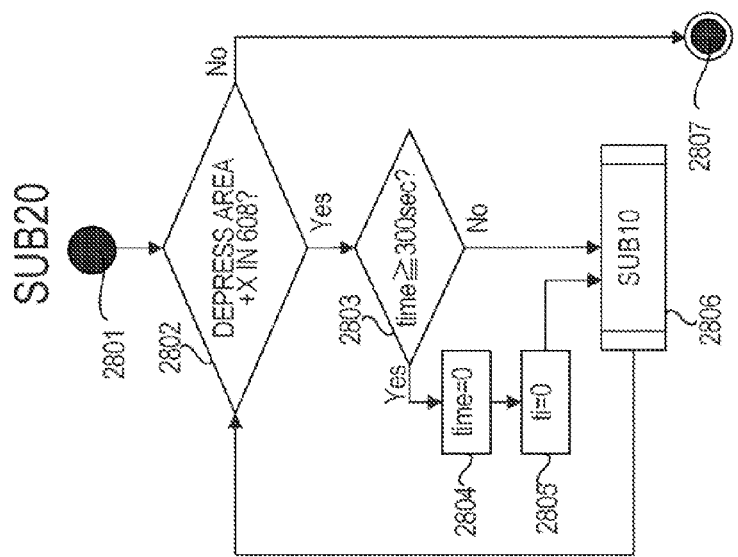
FIG. 28 is an activity diagram illustrating an operation of a predefined process SUB20.

FIG. 28 illustrates the predefined process SUB20, which defines an operation when the area of X>0 on the double-dot dashed line 608 of the GUI illustrated in FIG. 6 is depressed. Step 2801 is an initial state of the activity of the predefined process SUB20. Step 2802 is a determination section for determining whether or not the area of X>0 on the double-dot dashed line 608 of the GUI illustrated in FIG. 6 is depressed. If the area of X>0 on the double-dot dashed line 608 is depressed, the process proceeds to Step 2803. Step 2803 is a determination section for determining whether or not a value of the timer counter is 300 seconds or larger. If the value of the timer counter is 300 seconds or larger, the process proceeds to Steps 2804, 2805, and 2806. In Step 2804, the timer counter is reset to zero. In Step 2805, ti is reset to zero. This variable ti is described later with reference to FIGS. 32 and 33. In Step 2806, a predefined process SUB10 is performed. The predefined process SUB10 is described after description of the predefined process SUB20. If the timer counter value is smaller than 300 seconds, the process proceeds to Step 2806. When the process of Step 2806 is finished, the process returns to Step 2802. If the area of X>0 on the double-dot dashed line 608 of the GUI illustrated in FIG. 6 is not depressed, the process proceeds to Step 2807. Step 2807 is a state where the activity of the predefined process SUB20 is finished.

Figure 18:
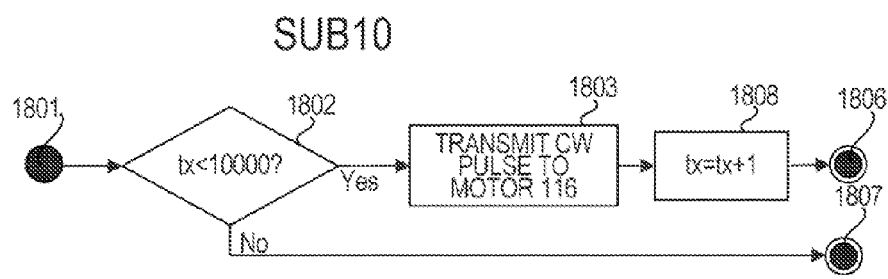
FIG. 18 is an activity diagram illustrating an operation of a predefined process SUB10.

FIG. 18 illustrates the predefined process SUB10. This predefined process is a process that is used for the predefined process SUB20 as described above. Step 1801 is an initial state of the activity of the predefined process SUB10. Step 1802 is a determination section for determining whether or not tz is smaller than 10,000, that is, whether or not the position of the optical head portion 105 is other than the stroke limit position in the positive direction of the X axis. If the position of the optical head portion 105 in the X axis direction is other than the stroke limit position in the positive direction of the X axis, the process proceeds to Step 1803. In Step 1803, the CW pulse is sent to the motor 116. Then, the process proceeds to next Step 1808. In Step 1808, one is added to tz. Then, the process proceeds to next Step 1806. Step 1806 is a state where the activity of the predefined process SUB10 is finished. If tx is 10,000, that is, the optical head portion 105 is at the stroke limit position in the positive direction of the X axis, the process proceeds to Step 1807. Step 1807 is a state where the activity of the predefined process SUB10 is finished.

Figure 29:
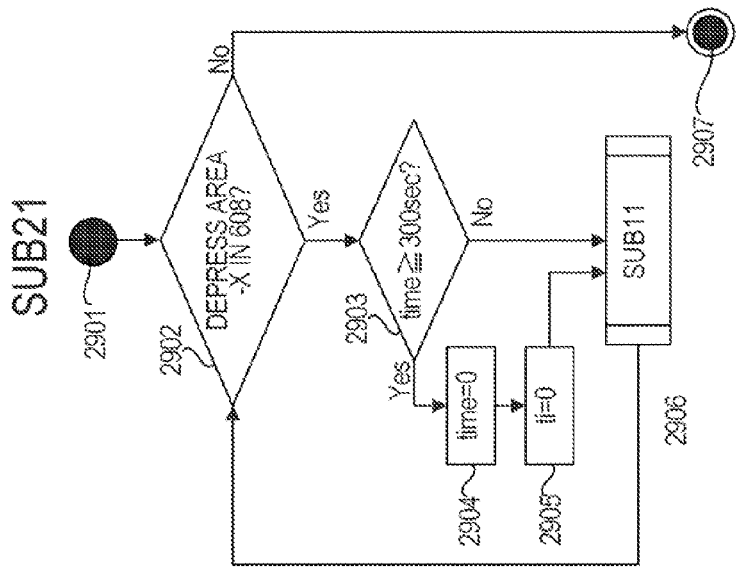
FIG. 29 is an activity diagram illustrating an operation of a predefined process SUB21.

FIG. 29 illustrates the predefined process SUB21, which defines an operation when the area of X<0 on the double-dot dashed line 608 of the GUI illustrated in FIG. 6 is depressed. Step 2901 is an initial state of the activity of the predefined process SUB21. Step 2902 is a determination section for determining whether or not the area of X<0 on the double-dot dashed line 608 of the GUI illustrated in FIG. 6 is depressed. If the area is depressed, the process proceeds to Step 2903. Step 2903 is a determination section for determining whether or not a value of the timer counter is 300 seconds or larger. If the value of the timer counter is 300 seconds or larger, the process proceeds to Steps 2904, 2905, and 2906. In Step 2904, the timer counter is reset to zero. In Step 2905, ti is reset to zero. This variable ti is described later with reference to FIGS. 32 and 33. In Step 2906, a predefined process SUB11 is performed. The predefined process SUB11 is described after description of the predefined process SUB21. If the timer counter value is smaller than 300 seconds, the process proceeds to Step 2906. When the process of Step 2906 is finished, the process returns to Step 2902. If the area of X<0 on the double-dot dashed line 608 of the GUI illustrated in FIG. 6 is not depressed, the process proceeds to Step 2907. Step 2907 is a state where the activity of the predefined process SUB21 is finished.

Figure 19:
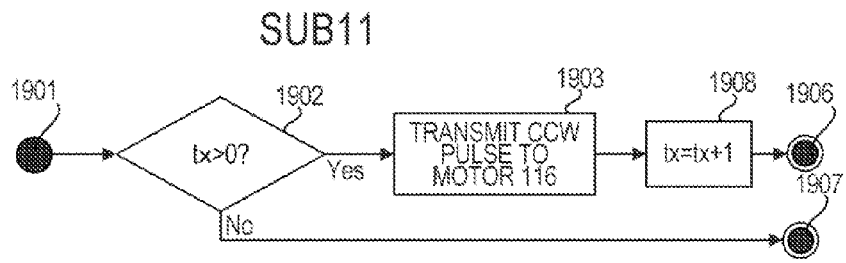
FIG. 19 is an activity diagram illustrating an operation of a predefined process SUB11.

FIG. 19 illustrates the predefined process SUB11. This predefined process is a process that is used for the predefined process SUB21 as described above. Step 1901 is an initial state of the activity of the predefined process SUB11. Step 1902 is a determination section for determining whether or not tx is larger than 0, that is, whether or not the position of the optical head portion 105 is other than the origin of the X axis. If the position of the optical head portion 105 in the X axis direction is other than the origin, the process proceeds to Step 1903. In Step 1903, the CCW pulse is sent to the motor 116. Then, the process proceeds to next Step 1908. In Step 1908, one is added to tx. Then, the process proceeds to next Step 1906. Step 1906 is a state where the activity of the predefined process SUB11 is finished. If tx is 0, that is, the optical head portion 105 is at the origin of the X axis, the process proceeds to Step 1907. Step 1907 is a state where the activity of the predefined process SUB11 is finished.

Figure 30:
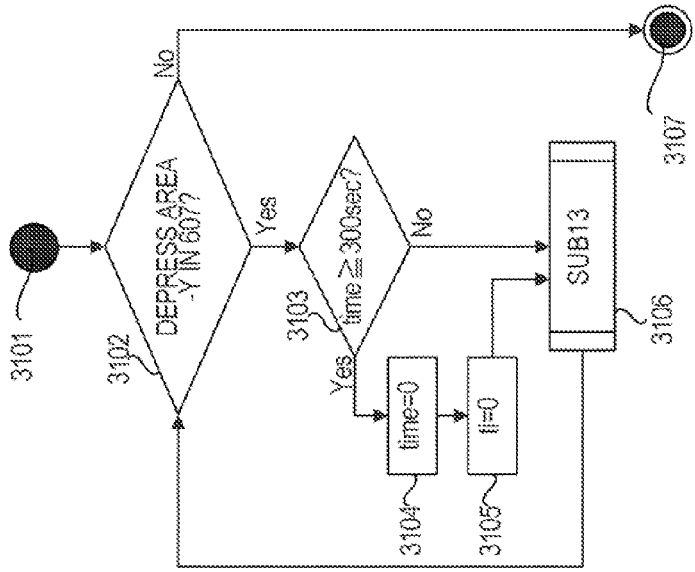
FIG. 30 is an activity diagram illustrating an operation of a predefined process SUB22.

FIG. 30 illustrates the predefined process SUB22, which defines an operation when the area of Y>0 on the double-dot dashed line 607 of the GUI illustrated in FIG. 6 is depressed. Step 3001 is an initial state of the activity of the predefined process SUB22. Step 3002 is a determination section for determining whether or not the area of Y>0 on the double-dot dashed line 607 of the GUI illustrated in FIG. 6 is depressed. If the area is depressed, the process proceeds to Step 3003. Step 3003 is a determination section for determining whether or not a value of the timer counter is 300 seconds or larger. If the value of the timer counter is 300 seconds or larger, the process proceeds to Steps 3004, 3005, and 3006. In Step 3004, the timer counter is reset to zero. In Step 3005, ti is reset to zero. This variable ti is described later with reference to FIGS. 32 and 33. In Step 3006, a predefined process SUB12 is performed. The predefined process SUB12 is described after description of the predefined process SUB22. If the timer counter value is smaller than 300 seconds, the process proceeds to Step 3006. When the process of Step 3006 is finished, the process returns to Step 3002. If the area of Y>0 on the double-dot dashed line 607 of the GUI illustrated in FIG. 6 is not depressed, the process proceeds to Step 3007. Step 3007 is a state where the activity of the predefined process SUB22 is finished.

Figure 20:
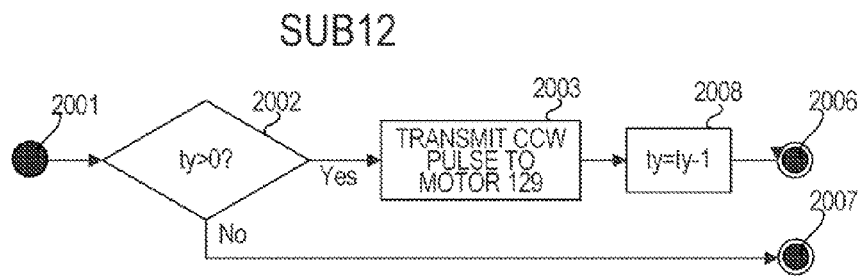
FIG. 20 is an activity diagram illustrating an operation of a predefined process SUB12.

FIG. 20 illustrates the predefined process SUB12. This predefined process is a process that is used for the predefined process SUB22 as described above. Step 2001 is an initial state of the activity of the predefined process SUB12. Step 2002 is a determination section for determining whether or not ty is larger than 0, that is, whether or not the position of the optical head portion 105 is other than the origin of the Y axis. If the position of the optical head portion 105 in the Y axis direction is other than the origin, the process proceeds to Step 2003. In Step 2003, the CCW pulse is sent to the motor 129. Then, the process proceeds to next Step 2008. In Step 2008, one is subtracted from ty. Then, the process proceeds to next Step 2006. Step 2006 is a state where the activity of the predefined process SUB12 is finished. If ty is 0, that is, the optical head portion 105 is at the origin of the Y axis, the process proceeds to Step 2007. Step 2007 is a state where the activity of the predefined process SUB12 is finished.

Figure 31:
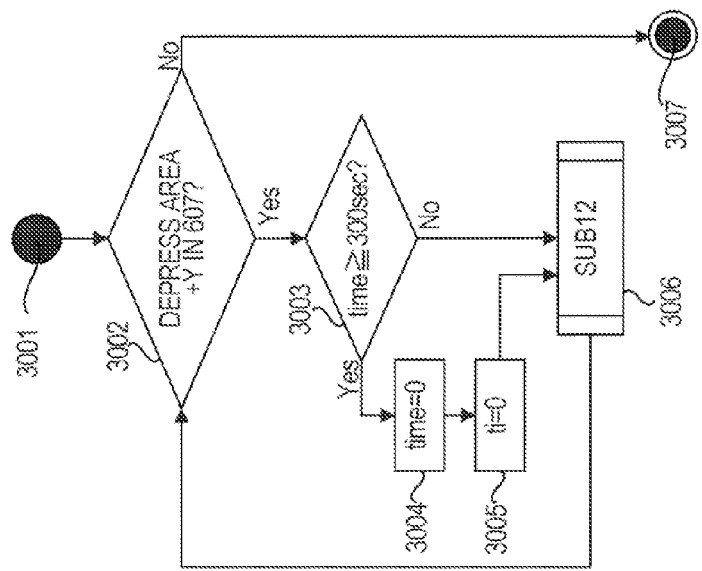
FIG. 31 is an activity diagram illustrating an operation of a predefined process SUB23.

FIG. 31 illustrates the predefined process SUB23, which defines an operation when the area of Y<0 on the double-dot dashed line 607 of the GUI illustrated in FIG. 6 is depressed.

Step 3101 is an initial state of the activity of the predefined process SUB23. Step 3102 is a determination section for determining whether or not the area of Y<0 on the double-dot dashed line 607 of the GUI illustrated in FIG. 6 is depressed. If the area is depressed, the process proceeds to Step 3103. Step 3103 is a determination section for determining whether or not a value of the timer counter is 300 seconds or larger. If the value of the timer counter is 300 seconds or larger, the process proceeds to Steps 3104, 3105, and 3106. In Step 3104, the timer counter is reset to zero. In Step 3105, ti is reset to zero. This variable ti is described later with reference to FIGS. 32 and 33. In Step 3106, a predefined process SUB13 is performed. The predefined process SUB13 is described after description of the predefined process SUB23. If the timer counter value is smaller than 300 seconds, the process proceeds to Step 3106. When the process of Step 3106 is finished, the process returns to Step 3102. If the area of Y<0 on the double-dot dashed line 607 of the GUI illustrated in FIG. 6 is not depressed, the process proceeds to Step 3107. Step 3107 is a state where the activity of the predefined process SUB23 is finished.

Figure 21:
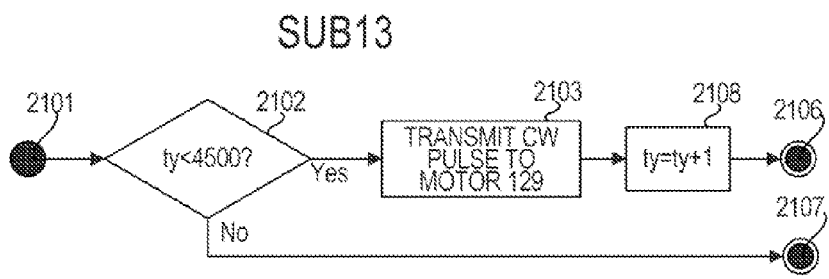
FIG. 21 is an activity diagram illustrating an operation of a predefined process SUB13.

FIG. 21 illustrates the predefined process SUB13. This predefined process is a process that is used for the predefined process SUB23 as described above. Step 2101 is an initial state of the activity of the predefined process SUB13. Step 2102 is a determination section for determining whether or not ty is smaller than 4,500, that is, whether or not the position of the optical head portion 105 is other than the stroke limit position in the negative direction of the Y axis. If the position of the optical head portion 105 in the Y axis direction is other than the stroke limit position in the negative direction of the Y axis, the process proceeds to Step 2103. In Step 2103, the CW pulse is sent to the motor 129. Then, the process proceeds to next Step 2108. In Step 2108, one is added to ty. Then, the process proceeds to next Step 2106. Step 2106 is a state where the activity of the predefined process SUB13 is finished. If ty is 4,500, that is, the optical head portion 105 is at the stroke limit position in the negative direction of the Y axis, the process proceeds to Step 2107. Step 2107 is a state where the activity of the predefined process SUB13 is finished.

Figure 32:
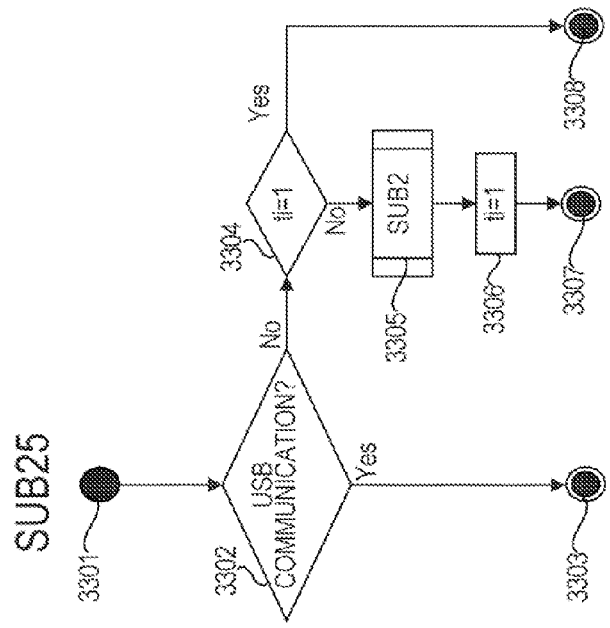
FIG. 32 is an activity diagram illustrating an operation of a predefined process SUB24.

FIG. 32 illustrates the predefined process SUB24. This predefined process defines a process for changing the attitude of the optical head portion 105 to the attitude for packing if the GUI is not operated for 300 seconds or larger. Step 3201 is an initial state of the activity of the predefined process SUB24. In Step 3202, a time counter value is read from the real time clock circuit of the CPU unit 136. Step 3203 is a determination section for determining whether or not the time counter value is 300 seconds or larger. If the time counter value is 300 seconds or larger, the process proceeds to Step 3205. In Step 3205, it is determined whether or not ti is one. If ti is one, the process proceeds to Step 3209. Step 3209 is a state where the activity of the predefined process SUB24 is finished. If ti is not one, the process proceeds to Step 3206. In Step 3206, the predefined process SUB2 is performed. As described above, the predefined process SUB2 performs the process of changing the attitude of the optical head portion 105 to the attitude for packing. Then, next Step 3207 is performed. In Step 3207, ti is set to one. Then, the process proceeds to Step 3208. If ti is one, the predefined process SUB2 for changing the attitude to the attitude for packing is not called unless the GUI of FIG. 5 is operated in the next parallel processing loop of Step 806 and subsequent steps of FIG. 8 so that the optical head portion 105 is moved. If the time counter value is smaller than 300 seconds, the process proceeds to Step 3204. Steps 3204 and 3208 are a state where the activity of the predefined process SUB24 is finished.

In other words, in this predefined process, if a first period is measured while it is determined that there is no communication of an operation signal from the PC to the ophthalmologic apparatus (the optical head portion 105 and the chin rest unit portion 107), the sub control apparatus in the CPU unit 136 performs the drive to an examination waiting position (second predetermined position) of the ophthalmologic apparatus. In addition, if a second period longer than the first period is measured, the sub control apparatus performs the drive to the packing position (first predetermined position) of the ophthalmologic apparatus. An example of this examination waiting position is a position of the chin rest unit portion 107 having a height at which the eye to be inspected of a standard patient can be observed with respect to the optical head portion 105 at an examination start position. In addition, as to the optical head portion 105, positions in the Z axis direction that are set in accordance with an examination item and an object to be photographed are examples of the examination waiting position.

Figure 33:
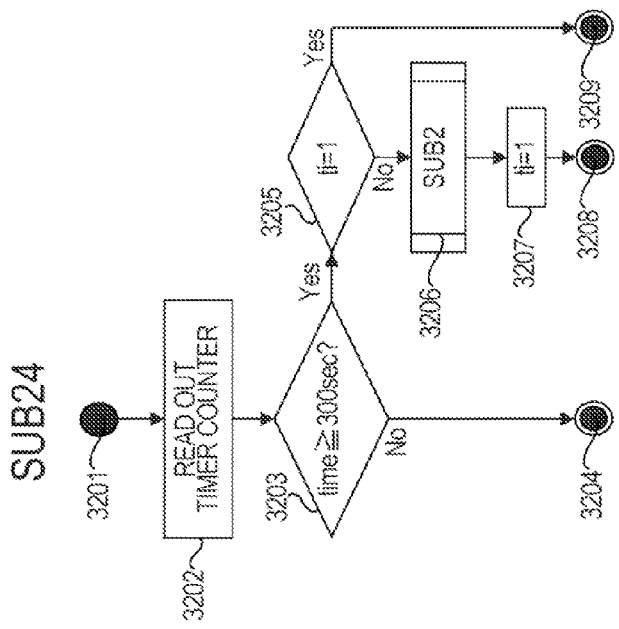
FIG. 33 is an activity diagram illustrating an operation of a predefined process SUB25.

FIG. 33 illustrates the predefined process SUB25. This predefined process defines a process for changing an attitude of the optical head portion 105 to the attitude for packing when the USB communication between the ophthalmologic apparatus of FIGS. 1A and 1B and the PC 156 is stopped. Step 3301 is an initial state of the activity of the predefined process SUB25. Step 3302 is a determination section for determining whether or not USB communication is established between the ophthalmologic apparatus of FIGS. 1A and 1B and the PC 156. If the USB communication is established, the process proceeds to Step 3303. If the USB communication is not established, the process proceeds to Step 3304. In Step 3304, it is determined whether or not ti is one. If ti is one, the process proceeds to Step 3308. If ti is not one, the process proceeds to Step 3305. In Step 3305, the predefined process SUB2 is performed. As described above, the predefined process SUB2 performs the process of changing the attitude of the optical head portion 105 to the attitude for packing. Then, next Step 3306 is performed. In Step 3306, ti is set to one. Then, the process proceeds to Step 3307. If ti is one, the predefined process SUB2 for changing the attitude to the attitude for packing is not called unless the GUI of FIG. 5 is operated in the next parallel processing loop of Step 806 and subsequent steps of FIG. 8 so that the optical head portion 105 is moved. Steps 3303, 3307, and 3308 are a state where the activity of the predefined process SUB25 is finished.

As described above, if the USB communication between the PC 156 for control and the main body of the ophthalmologic apparatus of FIGS. 1A and 1B is established, an attitude of the optical head portion 105 becomes the attitude for waiting eye examination. In addition, if the USB communication between the PC 156 for control and the main body of the ophthalmologic apparatus of FIGS. 1A and 1B is not established, when the power supply is changed from OFF to ON, an attitude of the optical head portion 105 is changed to the attitude for packing. In addition, if the GUI is not used for a certain period of time, an attitude of the optical head portion 105 is changed to the attitude for packing.

In other words, in this case, a communication status between the ophthalmologic apparatus and the PC 156 for control is determined, and in accordance with a result of the determination of the communication status, the CPU unit 136 (sub control apparatus) of the ophthalmologic apparatus drives the optical head portion 105 and the chin rest unit portion 107 to one of the packing position and the examination waiting position different from the packing position. More specifically, a module region that functions as an on-off determination unit in the CPU unit 136 determines whether the power of the ophthalmologic apparatus is turned on or off, and further, the sub control apparatus reserves the power off operation for a preset period in accordance with the determination of power off so as to drive the ophthalmologic apparatus to the packing position. In addition, a module region that functions as a communication determination unit in the CPU unit 136 determines whether or not the communication status between the PC 156 for control and the ophthalmologic apparatus is secured. If it is determined that the communication status is not secured, the power off operation and the driving to the packing position of the ophthalmologic apparatus are performed.

These indicate that the attitude is efficiently changed to the attitude for packing when performing packing. The communication is the USB communication in the description of this embodiment, but any communication can be adopted, such as communication using a wireless LAN or a coaxial cable.

In other words, the ophthalmologic apparatus according to the present invention includes a unit for controlling the attitude of the main body by the PC for control, and a unit for electrically driving a drive shaft of the main body and a chin rest. If the power supply for the main body is changed from OFF to ON in a state where communication between the PC for control and the main body is not established, the attitude becomes the attitude for packing. If the communication between the PC for control and the main body is established, the attitude becomes the attitude for waiting eye examination.

Alternatively, the ophthalmologic apparatus includes the unit for controlling the attitude of the main body by the PC for control, the unit for electrically driving the drive shaft of the main body and the chin rest, a power turn-off unit, and a power turn-off delay unit. When the power of the main body is turned off, the attitude becomes the attitude for packing.

Further, the ophthalmologic apparatus includes the unit for controlling the attitude of the main body by the PC for control, the unit for electrically driving the drive shaft of the main body and the chin rest, and a unit for detecting a period of time in which there is no operation signal. If there is no operation signal for a certain period of time, the positioning is performed at a position for waiting eye examination. After positioning the attitude at the position for waiting eye examination, if the operation signal is not received for a certain period of time, the positioning is performed at the attitude for packing.

Second Embodiment

An ophthalmologic apparatus of a second embodiment of the present invention is described with reference to FIG. 34.

Compared with the ophthalmologic apparatus of the first embodiment, the ophthalmologic apparatus of the second embodiment has the following additional configuration. A battery 3403 is disposed between the CPU unit 136 and the power supply unit 138. An electric signal when the AC power supply input to the power supply unit is cut off is sent to the CPU unit. The CPU unit receives an AC cut off signal sent from the power supply unit and operates the XYZ unit 108 to change the attitude to the attitude for packing.

Figure 34:
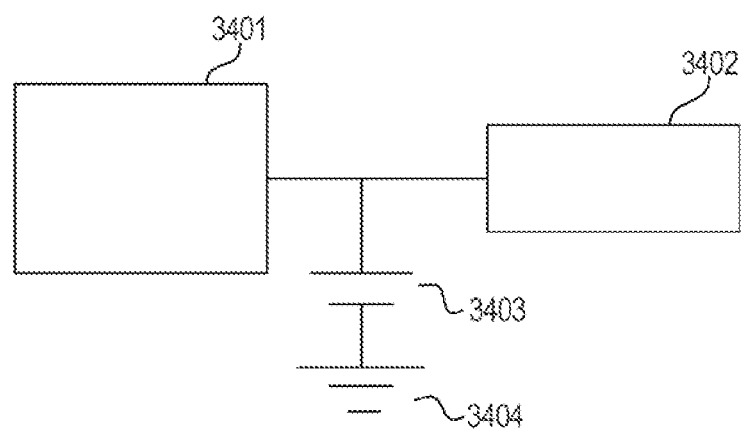
FIG. 34 is a block diagram illustrating an ophthalmologic apparatus according to a second embodiment of the present invention, which illustrates a difference from the ophthalmologic apparatus according to the first embodiment.

A block diagram of FIG. 34 illustrates a part of this embodiment, which is different from the first embodiment illustrated in the block diagrams of FIGS. 1A, 1B and 2. A CPU unit 3401 corresponds to reference numeral 136 of the first embodiment. A power supply unit 3402 corresponds to reference numeral 138 of the first embodiment. The battery 3403 is a 24 V battery. The battery 3403 is connected to a ground 3404. Other structures are the same.

If the power switch 150 is turned on, the battery 3403 is charged. When the power switch 150 is turned off, the battery 3403 supplies power to the CPU unit 3401. In this case, the power supply unit 3402 sends to the CPU unit 3401 a signal indicating that the AC power supply is cut off. When the CPU unit 3401 receives the signal, the CPU unit 3401 changes the attitude of the optical head portion 105 to the attitude for packing.

Figure 35:
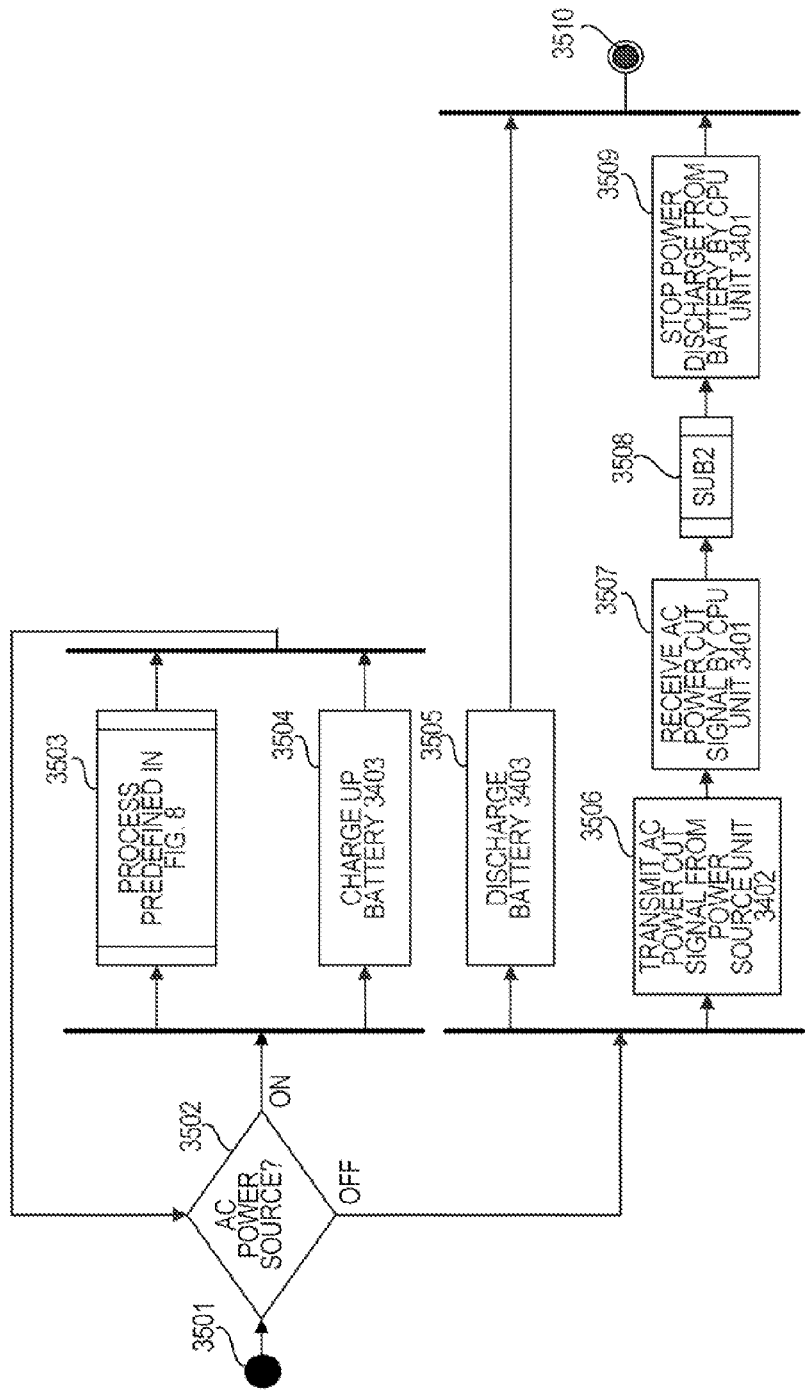
FIG. 35 is an activity diagram of the ophthalmologic apparatus according to the second embodiment.

FIG. 35 is an activity diagram of the second embodiment. Step 3501 is an initial state of the activity diagram. Step 3502 is a determination section for determining whether or not the power is turned on. If the power is turned on, Step 3503 and Step 3504 are processed in parallel. Step 3503 is the process of FIG. 8 described above in the first embodiment. Step 3504 is a process for charging the battery 3403. When this process is finished, the process returns to Step 3502 so as to repeat the loop process as long as the AC power is turned on. If the AC power is turned off, the processes of Step 3505 and Steps 3506 to 3509 are processed in parallel. Step 3505 is a process of discharging the battery 3403. In Step 3506, the power supply unit 3402 sends out the AC cut off signal. In Step 3507, the CPU unit receives the AC cut off signal. In Step 3508, the predefined process of FIG. 10 described above in the first embodiment is performed. This process is a process for changing the attitude of the optical head portion 105 to the attitude for packing. In Step 3509, the CPU unit 3401 cuts off discharge of the battery 3403. When these parallel processes are finished, the process proceeds to Step 3510. Step 3510 is a state where the activity is finished.

According to the embodiments described above, when the power switch is turned off, the attitude of the optical head portion 105 becomes the attitude for packing. Therefore, time loss in packing or transporting can be decreased.

OTHER EMBODIMENT

Further, the present invention may also be realized by executing the following process. Specifically, software (program) for realizing the functions of the embodiments described above is supplied to a system or an apparatus via a network or an arbitrary type of storage medium, and a computer (CPU or MPU) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-190585, filed Aug. 30, 2012, which is hereby incorporated by reference herein in its entirety.

What is claimed is:

1. An ophthalmologic apparatus, which is to be controlled by a separable control device, the ophthalmologic apparatus comprising:

an optical head unit portion for photographing an image of an eye to be inspected in accordance with a command from the control device;

an optical head unit drive portion for driving the optical head unit portion with respect to the eye to be inspected;

a chin rest unit portion for defining a height of the eye to be inspected in accordance with a command from the control device;

a chin rest unit drive portion for driving the chin rest unit portion with respect to the optical head unit portion;

a sub control apparatus different from the control device; and a status determination unit for determining a status of the ophthalmologic apparatus, wherein the sub control apparatus controls, in accordance with a result of the determination by the status determination unit, the optical head unit drive portion and the chin rest unit drive portion to drive the optical head unit portion and the chin rest unit portion to one of a first predetermined position and a second predetermined position different from the first predetermined position.

2. An ophthalmologic apparatus according to claim 1, wherein:

the status determination unit comprises an on-off determination unit for determining whether power of the ophthalmologic apparatus is turned on or off, and a timer; and the sub control apparatus reserves a power off operation for a preset period by the timer in accordance with the determination of power off by the on-off determination unit, so as to drive the optical head unit portion and the chin rest unit portion to the first predetermined position.

3. An ophthalmologic apparatus according to claim 1, wherein:

the status determination unit comprises a communication determination unit for determining whether or not a communication status between the control device and the ophthalmologic apparatus is secured; and when the communication determination unit determines that the communication status is not secured, the sub control apparatus drives the optical head unit portion and the chin rest unit portion to the first predetermined position.

4. An ophthalmologic apparatus according to claim 1, wherein:

the status determination unit comprises a timer;

when the timer counts a first period under a state where the status determination unit determines that there is no communication of an operation signal from the control device to the ophthalmologic apparatus, the sub control apparatus drives the optical head unit portion and the chin rest unit portion to the second predetermined position; and when the timer counts a second period that is longer than the first period, the sub control apparatus drives the optical head unit portion and the chin rest unit portion to the first predetermined position.

5. A control method for an ophthalmologic apparatus that is to be controlled by a separable control device and includes an optical head unit portion for photographing an image of an eye to be inspected and a chin rest unit portion for defining a height of the eye to be inspected with respect to the optical head unit portion when photographing, the control method comprising:

determining a communication status between the ophthalmologic apparatus and the control device; and driving, by a sub control apparatus of the ophthalmologic apparatus, the optical head unit portion and the chin rest unit portion to one of a first predetermined position and a second predetermined position different from the first predetermined position in accordance with a result of the determination of the communication status.

6. A control method for an ophthalmologic apparatus according to claim 5, further comprising:

determining whether power of the ophthalmologic apparatus is turned on or off; and reserving, by the sub control apparatus, a power off operation for a preset period in accordance with the determination of power off by an on-off determination unit, so as to drive the optical head unit portion and the chin rest unit portion to the first predetermined position.

7. A control method for an ophthalmologic apparatus according to claim 5, further comprising:

determining whether or not the communication status between the control device and the ophthalmologic apparatus is secured; and driving, by the sub control apparatus, the optical head unit portion and the chin rest unit portion to the first predetermined position, when it is determined that the communication status is not secured.

8. A control method for an ophthalmologic apparatus according to claim 5, further comprising:

driving, by the sub control apparatus, the optical head unit portion and the chin rest unit portion to the second predetermined position when a first period is measured under a state where it is determined that there is no communication of an operation signal from the control device to the ophthalmologic apparatus; and driving, by the sub control apparatus, the optical head unit portion and the chin rest unit portion to the first predetermined position when a second period that is longer than the first period is measured.

9. A program for causing a computer to perform steps of the control method for an ophthalmologic apparatus according to claim 5.

* * * * *